(12) United States Patent
Wang et al.

(10) Patent No.: US 12,270,883 B2
(45) Date of Patent: *Apr. 8, 2025

(54) SPARSE REPRESENTATION OF MEASUREMENTS

(71) Applicant: Q Bio, Inc., San Carlos, CA (US)

(72) Inventors: Guanhua Wang, Ann Arbor, MI (US); Matteo Alessandro Francavilla, San Mateo, CA (US); Thomas Witzel, Redwood City, CA (US); Jeffrey H. Kaditz, Wilson, WY (US)

(73) Assignee: Q Bio, Inc., San Carlos, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 18/172,619

(22) Filed: Feb. 22, 2023

(65) Prior Publication Data
US 2023/0204700 A1 Jun. 29, 2023

Related U.S. Application Data

(63) Continuation of application No. 17/510,258, filed on Oct. 25, 2021, now Pat. No. 11,614,508.

(51) Int. Cl.
*G01R 33/56* (2006.01)
*A61B 5/055* (2006.01)
(Continued)

(52) U.S. Cl.
CPC .......... *G01R 33/5608* (2013.01); *A61B 5/055* (2013.01); *G01R 33/5611* (2013.01);
(Continued)

(58) Field of Classification Search
CPC .......................... A61B 5/055; G01R 33/5608; G01R 33/5611; G06T 7/0012; G06T 2207/10088; G06T 2207/20081
See application file for complete search history.

(56) References Cited

U.S. PATENT DOCUMENTS 4,729,892 A 3/1988 Beall
5,486,762 A 1/1996 Freedman et al.
(Continued)

FOREIGN PATENT DOCUMENTS

CN 102947721 2/2013
CN 110140042 8/2019
(Continued)

OTHER PUBLICATIONS

"Cohen Ouri et al, "Deep learning for fast MR Fingerprinting Reconstruction", Proc. Inti. Soc. Mag. Reson. Med. 25, Apr. 7, 2017".
(Continued)

*Primary Examiner* — Gregory H Curran
(74) *Attorney, Agent, or Firm* — Aurora Consulting LLC; Steven E. Stupp; Ashley Sloat

(57) ABSTRACT

A computer system that performs a sparsity technique is described. During operation, the computer system accesses or obtains information associated with non-invasive measurements performed on at least an individual, historical non-invasive measurements, and a dictionary of predetermined features or basis functions associated with the historical non-invasive measurements. Note that the non-invasive measurements and the historical non-invasive measurements may include or correspond to magnetic resonance (MR) measurements. For example, the MR measurements may include magnetic resonance imaging (MRI) scans. Then, the computer system updates the dictionary of predetermined features based at least in part on the non-invasive measurements and the historical non-invasive measurements, where the updating includes performing a minimization technique with a cost function having an L2-norm term and an L0-norm term. Next, the computer system determines weights associated with features in the updated
(Continued)

dictionary of predetermined features based at least in part on the non-invasive measurements.

20 Claims, 16 Drawing Sheets

(51) Int. Cl.
    *G01R 33/561*     (2006.01)
    *G06T 7/00*     (2017.01)

(52) U.S. Cl.
    CPC .. *G06T 7/0012* (2013.01); *G06T 2207/10088* (2013.01); *G06T 2207/20081* (2013.01)

(56) References Cited

U.S. PATENT DOCUMENTS

| | | |
|---|---|---|
| 5,619,138 A | 4/1997 | Rourke |
| 5,793,210 A | 8/1998 | Pla |
| 5,865,177 A | 2/1999 | Segawa |
| 6,084,408 A | 7/2000 | Chen |
| 6,148,272 A | 11/2000 | Bergstrom |
| 6,392,409 B1 | 5/2002 | Chen |
| 6,528,998 B1 | 3/2003 | Maier |
| 6,605,942 B1 | 8/2003 | Warren |
| 6,678,669 B2 | 1/2004 | Lapointe |
| 7,423,430 B1 | 9/2008 | Bresler |
| 7,576,538 B2 | 8/2009 | Meersmann |
| 7,924,002 B2 | 4/2011 | Lu |
| 7,940,927 B2 | 5/2011 | Futa |
| 7,974,942 B2 | 7/2011 | Pomroy |
| 8,078,554 B2 | 12/2011 | Lambin |
| 8,108,311 B2 | 1/2012 | Herlitz |
| 8,427,157 B2 | 4/2013 | Schmitt |
| 8,432,165 B2 | 4/2013 | Weiger Senften |
| 8,502,532 B2 | 8/2013 | Assmann |
| 8,686,727 B2 | 4/2014 | Reddy |
| 8,723,518 B2 | 5/2014 | Seiberlich |
| 8,736,265 B2 | 5/2014 | Boernert |
| 9,046,589 B2 | 6/2015 | Gjesdal |
| 9,103,896 B2 | 8/2015 | Gross |
| 9,192,322 B2 | 11/2015 | Guo |
| 9,513,359 B2 | 12/2016 | Koch |
| 9,514,169 B2 | 12/2016 | Mattsson |
| 9,958,521 B2 | 5/2018 | Gettings |
| 9,977,106 B2 | 5/2018 | Eggers |
| 10,132,699 B1 | 11/2018 | Langlois |
| 10,132,899 B2 | 11/2018 | Yoshitaka |
| 10,402,910 B1 | 9/2019 | Scott |
| 10,571,542 B2 | 2/2020 | Sbrizzi et al. |
| 2001/0043068 A1 | 11/2001 | Lee |
| 2002/0155587 A1 | 10/2002 | Opalsky |
| 2002/0177771 A1 | 11/2002 | Guttman |
| 2003/0210043 A1 | 11/2003 | Freedman |
| 2004/0266442 A1 | 12/2004 | Hoglund |
| 2005/0054914 A1 | 3/2005 | Lewin |
| 2005/0096534 A1 | 5/2005 | Dumoulin |
| 2005/0137476 A1 | 6/2005 | Weiland |
| 2005/0181466 A1 | 8/2005 | Dambinova |
| 2005/0251023 A1 | 11/2005 | Kannengiesser et al. |
| 2008/0065665 A1 | 3/2008 | Pomroy |
| 2008/0081375 A1 | 4/2008 | Tesiram |
| 2008/0082834 A1 | 4/2008 | Mattsson |
| 2008/0129298 A1 | 6/2008 | Olson |
| 2008/0197844 A1 | 8/2008 | Ying |
| 2008/0292194 A1 | 11/2008 | Greiner |
| 2009/0240138 A1 | 9/2009 | Yi |
| 2009/0315561 A1 | 12/2009 | Assmann |
| 2010/0131518 A1 | 5/2010 | Elteto |
| 2010/0141252 A1 | 6/2010 | Schmitt |
| 2010/0142823 A1 | 6/2010 | Wang |
| 2010/0177188 A1 | 7/2010 | Kishima |
| 2010/0189328 A1 | 7/2010 | Boernert |
| 2010/0244827 A1 | 9/2010 | Hennel |
| 2010/0256496 A1 | 10/2010 | Zhu |
| 2010/0306854 A1 | 12/2010 | Neergaard |
| 2011/0004071 A1 | 1/2011 | Faiola |
| 2011/0044524 A1 | 2/2011 | Wang |
| 2011/0093243 A1 | 4/2011 | Tawhai |
| 2011/0095759 A1 | 4/2011 | Bhattacharya |
| 2011/0166484 A1 | 7/2011 | Virta |
| 2011/0254549 A1 | 10/2011 | Lin |
| 2012/0124161 A1 | 5/2012 | Tidwell |
| 2012/0177128 A1 | 7/2012 | Elad |
| 2012/0223707 A1 | 9/2012 | Gross |
| 2012/0271157 A1 | 10/2012 | Guo |
| 2013/0099786 A1 | 4/2013 | Huang |
| 2013/0271133 A1 | 10/2013 | Moeller |
| 2013/0275718 A1 | 10/2013 | Ueda |
| 2013/0294669 A1 | 11/2013 | El-Baz |
| 2013/0338930 A1 | 12/2013 | Senegas |
| 2014/0039300 A1 | 2/2014 | Gjesdal |
| 2014/0062475 A1 | 3/2014 | Koch |
| 2014/0107469 A1 | 4/2014 | Gjesdal |
| 2014/0336998 A1 | 11/2014 | Cecchi |
| 2015/0002149 A1 | 1/2015 | Nehrke et al. |
| 2015/0003706 A1 | 1/2015 | Eftestøl |
| 2015/0032421 A1 | 1/2015 | Dean |
| 2015/0040225 A1 | 2/2015 | Coates |
| 2015/0070013 A1 | 3/2015 | Schmidt |
| 2015/0089574 A1 | 3/2015 | Mattsson |
| 2015/0370904 A1 | 12/2015 | Joshi |
| 2016/0007968 A1 | 1/2016 | Sinkus |
| 2016/0077182 A1 | 3/2016 | Wang |
| 2016/0127123 A1 | 5/2016 | Johnson |
| 2016/0166209 A1 | 6/2016 | Sharma |
| 2016/0245882 A1 | 8/2016 | Popescu |
| 2017/0003365 A1 | 1/2017 | Rosen |
| 2017/0007148 A1 | 1/2017 | Gettings |
| 2017/0011255 A1 | 1/2017 | Gettings |
| 2017/0011514 A1 | 1/2017 | Westerhoff |
| 2017/0038452 A1 | 2/2017 | Trzasko |
| 2017/0123029 A1 | 5/2017 | Bhat et al. |
| 2017/0285122 A1 | 10/2017 | Deepak |
| 2017/0285123 A1 | 10/2017 | Kaditz |
| 2018/0120402 A1 | 5/2018 | Nehrke |
| 2018/0217073 A1 | 8/2018 | Zhao |
| 2018/0238983 A1 | 8/2018 | Cohen |
| 2018/0321347 A1 | 11/2018 | Wang |
| 2019/0056471 A1 | 2/2019 | Hutchinson |
| 2019/0294992 A1 | 9/2019 | Zhu |
| 2019/0383889 A1 | 12/2019 | Ding |
| 2020/0026967 A1 | 1/2020 | Kartoun et al. |
| 2020/0085382 A1 | 3/2020 | Taerum |
| 2020/0249300 A1 | 7/2020 | Lai |
| 2020/0249302 A1 | 8/2020 | Van Den Brink |
| 2020/0264249 A1 | 8/2020 | Tayli et al. |
| 2020/0289019 A1 | 9/2020 | Sacolick |
| 2020/0319283 A1 | 10/2020 | Wang |
| 2021/0096203 A1 | 9/2021 | Doruk |
| 2022/0163611 A1 | 5/2022 | Van Der Heide et al. |
| 2022/0236358 A1 | 7/2022 | Bernstein |
| 2022/0326330 A1 | 10/2022 | Farman |
| 2023/0044166 A1 | 2/2023 | Liu et al. |

FOREIGN PATENT DOCUMENTS

| | | |
|---|---|---|
| EP | 1953580 | 9/2014 |
| EP | 15001457.9 | 5/2015 |
| EP | 15020075.6 | 5/2015 |
| EP | 15171708.9 | 6/2015 |
| EP | 3093677 | 11/2016 |
| EP | 3093677 A1 | 11/2016 |
| JP | 2013029499 | 2/2013 |
| WO | 2014047326 | 3/2014 |
| WO | 2014205275 | 12/2014 |
| WO | 2015183792 | 12/2015 |
| WO | 2016073985 | 5/2016 |
| WO | 2016184779 A1 | 11/2016 |
| WO | 2017007663 | 1/2017 |

(56) References Cited

FOREIGN PATENT DOCUMENTS

| WO | 2017210225 | 12/2017 |
|---|---|---|
| WO | 2022106299 A1 | 5/2022 |

OTHER PUBLICATIONS

Drescher et al., article titled "Longitudinal Screening Algorithm That Incorporates Change Over Time in CA125 Levels Identifies Ovarian Cancer Earlier Than a Single-Threshold Rule".

"Elisabeth Hoppe et al: Magnetic Resonance Fingerprinting: A New Approach for Predicting Quantitative Parameter Values from Time Series", German Medical Data Sciences: Visions and Bridges (62. Jahrestagung der GMDS), Sep. 17, 2017, pp. 202-206; Retrieved from the Internet: URL:https://www5.informatik.uni-erlangen.de/Forschung/Pub likationen/2017 /Hoppe17-DLF.pdf [retrieved on Dec. 11, 2018].

"European Application No. 20756501.1, European Extended Search Report mailed Oct. 20, 2022, 13 pages".

"G. Schultz, "Magnetic Resonance Imaging with Nonlinear Gradient Fields: Signal Encoding and Image Reconstruction" Springer Verlag, New York, 2013), Chapter 2, pp. 1-10.".

"Gualda et al. SPIM-fluid: open source light-sheet based platform for high-throughput imaging. Biomed Opt Express (Nov. 1, 2015} vol. 6, No. 11, pp. 4447-4456, p. 4448 para 2-3, p. 4450, para 2".

"Hasenkam et al., "Prosthetic Heart Valve Evaluation by Magnetic Resonance Imaging," European Journal of Cardio-thoracic Surgery 16 (1999) 300-305", 300-305.

"Hoppe Elisabeth et al: "Deep Learning for Magnetic Resonance Fingerprinting: Accelerating the Reconstruction of Quantitative Relaxation Maps", Proc. Inti. Soc. Mag. Reson. Med. 26 (2018), Jun. 1, 2018 Retrieved from the Internet: URL:https://cds.ismrm.org/protected/18MProceedings/PDFfiles/2791 .html [retrieved on Oct. 8, 2022]".

"Huttunen et al. "Solving Maxwell's equations using the ultra weak variational formulation." In: 1-32 Journal of Computational Physics. Jan. 18, 2006 (Jan. 18, 2006) Retrieved on Nov. 16, 2020 (Nov. 16, 2020) from <http://www.waveller.com/Waveller_Acoustics/publicationsfmaxwell_uwvf.pdf> entire document".

"I. Kononenko "Machine learning for medical diagnosis: history, state of the art and perspective" Artificial Intelligence in Medicine 23 (2001) 21 pgs ".

"International Application Serial No. PCT/US2016/040215, International Preliminary Report on Patentability and Written Opinion mailed Jan. 9, 2018".

"International Application Serial No. PCT/US2016/040215, International Search Report mailed Sep. 19, 2016", 2 pgs.

"International Application Serial No. PCT/US2016/040215, Written Opinion mailed Sep. 19, 2016", 9 pgs.

"International Application Serial No. PCT/US2016/040578, International Search Report mailed Sep. 19, 2016", 2 pgs.

"International Application Serial No. PCT/US2016/040578, Written Opinion mailed Sep. 19, 2016", 9 pgs.

"International Application Serial No. PCT/US2016/051204, International Search Report mailed Nov. 28, 2016", 2 pgs.

"International Application Serial No. PCT/US2016/051204, Written Opinion mailed Nov. 28, 2016", 10 pgs.

"International Application Serial No. PCT/US2017/022842, International Search Report mailed May 23, 2017", 2 pgs.

"International Application Serial No. PCT/US2017/022842, Written Opinion mailed on May 23, 2017", 4 pgs.

"International Application Serial No. PCT/US2017/022911, International Search Report mailed Jul. 19, 2017", 4 pgs.

"International Application Serial No. PCT/US2017/022911, Written Opinion mailed Jul. 19, 2017", 10 pgs.

"International Application Serial No. PCT/US2017/035071, International Search Report mailed Aug. 22, 2017", 2 pgs.

"International Application Serial No. PCT/US2017/035071, Written Opinion mailed Aug. 22, 2017", 7 pgs.

"International Application Serial No. PCT/US2017/035073, International Search Report mailed Aug. 11, 2017", 2 pgs.

"International Application Serial No. PCT/US2017/035073, Written Opinion mailed Aug. 11, 2017", 6 pgs.

"International Application Serial No. PCT/US2021/057136, International Search Report mailed Feb. 2, 2022".

"International Application Serial No. PCT/US2021/057136, Written Opinion mailed Feb. 2, 2022".

"International Application Serial No. PCT/US2022/029055, International Search Report mailed Aug. 30, 2022, 2 pages".

"International Application Serial No. PCT/US2022/029055, Written Opinion mailed Aug. 30, 2022, 6 pages".

"International Search Report mailed Feb. 24, 2021 in International Application No. PCT/US2020/052717, 2 pgs".

"Kwan et al: "MRI Simulation-Based Evaluation of Image-Processing and Classification Methods" IEEE Transactions on Medical Imaging. vol. 18 No. 11, Nov. 1999, ", 13 pgs.

"Nestares et al., "Robust Multiresolution Alignment of MRI Brain Volumes," Magnetic Resonance in Medicine 43:705-715 (2000)", 705-715.

"OURI Cohen et al., "MR fingerprinting Deep Reconstruction NEtwork (DRONE)", Arxiv.org, Cornell University Library, 201 Olin Library Cornell University Ithaca, NY 14853, Oct. 15, 2017".

"Patrick Virtue et al: Complex-valued Neural Nets for MRI Fingerprinting", Arxiv.org, Cornell University Library, 201 Olin Library Cornell University Ithaca, NY 14853, Jul. 1, 2017.

"Siemens. Magnetic Resonance Imaging. (Dec. 2012) [retrieved on Jun. 27, 2017, https://w5.siemens.com/web/ua/ru/medecine/detection_diagnosis/magnetic_resonans/035-15-MRI-scaners/Documents/mri-magnetom-family_brochure-00289718.pdf] p. 6-8, 13, 15-16".

"Thiesson Julien et al., "3D linear inversion of magnetic susceptibility data acquired by frequency domain EMI," Journal of Applied Geophysics (Year: 2016)".

"Vargas et al. "Object detection on compressive measurements using correlation filters and 1-20 sparse representation." Sep. 3, 2018 (Sep. 3, 2018) Retrieved on Dec. 31, 2021 (Dec. 31, 2021) from <https://ieeexplore .ieee.org/abstractldocument/8553312> entire document; 5 pages".

"Written Opinion mailed Feb. 24, 2021 in International Application No. PCT/US2020/052717, 5 pgs".

"Ying et al. "Joint image reconstruction and sensitivity estimation in SENSE (JSENSE)." In: 1-32 Magnetic Resonance in Medicine: An Official Journal of the International Society for Magnetic Resonance in Medicine. Feb. 21, 2007 (Feb. 21, 2007) Retrieved on Nov. 16, 2020(Nov. 16, 2020) from <https://onlinelibrary .wiley .com/doi/pdf/10.1002/mrm.21245> entire document".

"Ohliger et al., "Fundamental Physical Constraints on the Performance of Parallel Magnetic Resonance Imaging", International Society for Magnetic Resonance in Medicine, May 3, 2002 (May 3, 2002), p. 2387, XP040587120".

"Martin Uecker et al: "Image reconstruction by regularized nonlinear inversion—Joint estimation of coil sensitivities and image content", Magnetic Resonance in Medicine, vol. 60, No. 3, Aug. 5, 2008 (Aug. 5, 2008) , pp. 674-682, XP055007514, ISSN: 0740-3194, DOI: 10.1002/mrm.21691".

"Martin Uecker et al: "ESPIRIT—an eigenvalue approach to autocalibrating parallel MRI: Where SENSE meets GRAPPA", Magnetic Resonance in Medicine, vol. 71, No. 3, May 6, 2013 (May 6, 2013), pp. 990-1001, XP055357609, US ISSN: 0740-3194, DOI: 10.1002/mrm.24751".

"International Application Serial No. PCT/US2022/029055, International Preliminary Report on Patentability and Written Opinion mailed Jan. 4, 2024; 7 pages".

"European Application No. 20867684.1, European Extended Search Report mailed Sep. 28, 2023, 9 pages".

"Cohen O. et al., MR fingerprinting Deep Reconstruction NEtwork (DRONE). Magn Reson Med., Sep. 30, 2018, vol. 80, No. 3, pp. 885-894 Whole document Citation not enclosed due to copyright restrictions."

"Christian M Holme H et al: "ENLIVE: An Efficient Nonlinear Method for Calibrationless and Robust Parallel Imaging", Arxiv. org, Cornell University Library, 201 Olin Library Cornell University Ithaca, NY 14853, Jun. 29, 2017 (Jun. 29, 2017), XP080773543".

(56) References Cited

OTHER PUBLICATIONS

Ohliger et al., Ultimate Intrinsic Signal-to-Noise Ratio for Parallel MRI: Electromagnetic Field Considerations, Magnetic Resonance in Medicine 50:1018-1030 (2003).
Singapore Application Serial No. 11202108495X, Written Opinion mailed May 11, 2023.
International Application Serial No. PCT/US2021/057136, International Preliminary Report on Patentability mailed May 10, 2024.
M. Beister et al. Iterative reconstruction methods in X-ray CT, Physica Media. 28, pp. 94-108. (Year: 2012).
T. Humphries et al., Segmentation-Free Quasi-Newton Method for Polyenergetic CT reconstruction, IEEE. (Year: 2014); 5 pages.

SPARSE REPRESENTATION OF MEASUREMENTS

CROSS-REFERENCE TO RELATED APPLICATION

This application is a continuation of U.S. Non-Provisional application Ser. No. 17/510,258, entitled "SPARSE REPRESENTATION OF MEASUREMENTS," filed on Oct. 25, 2021, the contents of each of which are hereby incorporated by reference.

FIELD

The described embodiments relate generally to a sparse representation of measurements for use in image reconstruction and/or longitudinal analysis.

BACKGROUND

Many non-invasive characterization techniques are available for determining one or more physical parameters of a sample. For example, magnetic properties can be studied using magnetic resonance or MR (which is often referred to as 'nuclear magnetic resonance' or NMR), a physical phenomenon in which nuclei in a magnetic field absorb and re-emit electromagnetic radiation. Moreover, density variations and short or long-range periodic structures in solid or rigid materials can be studied using characterization techniques such as x-ray imaging, x-ray diffraction, computed tomography, neutron diffraction or electron microscopy, in which electromagnetic waves or energetic particles having small de Broglie wavelengths are absorbed or scattered by the sample. Furthermore, density variations and motion in soft materials or fluids can be studied using ultrasound imaging, in which ultrasonic waves are transmitted and reflected in the sample.

In each of these and other non-invasive characterization techniques, one or more external excitation (such as a flux of particles or incident radiation, static or time-varying scalar fields, and/or static or time-varying vector fields) are applied to the sample, and a resulting response of the sample, in the form a physical phenomenon, is measured to, directly or indirectly, determine the one or more physical parameters. As an example, in MR magnetic nuclear spins may be partially aligned (or polarized) in an applied external DC magnetic field. These nuclear spins may precess or rotate around the direction of the external magnetic field at an angular frequency (which is sometimes referred to as the 'Larmor frequency') given by the product of a gyromagnetic ratio of a type of nuclei and the magnitude or strength of the external magnetic field. By applying a perturbation to the polarized nuclear spins, such as one or more radio-frequency (RF) pulses (and, more generally, electro-magnetic pulses) having pulse widths corresponding to the angular frequency and at a right-angle or perpendicular to the direction of the external magnetic field, the polarization of the nuclear spins can be transiently changed. The resulting dynamic response of the nuclear spins (such as the time-varying total magnetization) can provide information about the physical and material properties of a sample, such as one or more physical parameters associated with the sample.

Moreover, in general each of the characterization techniques may allow one or more physical parameters to be determined in small volumes or voxels in a sample, which can be represented using a tensor. Using magnetic resonance imaging (MRI) as an example, the dependence of the angular frequency of precession of nuclear spins (such as protons or the isotope $^1$H) on the magnitude of the external magnetic field can be used to determine images of three-dimensional (3D) or anatomical structure and/or the chemical composition of different materials or types of tissue. In particular, by applying a non-uniform or spatially varying magnetic field to a sample, the resulting variation in the angular frequency of precession of $^1$H spins is typically used to spatially localize the measured dynamic response of the $^1$H spins to voxels, which can be used to generate images, such as of the internal anatomy of a patient.

However, the characterization of the physical properties of a sample is often time-consuming, complicated and expensive. For example, acquiring MR images in MRI with high-spatial resolution (i.e., small voxels sizes) often involves a large number of measurements (which are sometimes referred to as 'scans') to be performed for time durations that are longer than the relaxation times of the $^1$H spins in different types of tissue in a patient. Moreover, in order to achieve high-spatial resolution, a large homogenous external magnetic field is usually used during MRI. The external magnetic field is typically generated using a superconducting magnet having a toroidal shape with a narrow bore, which can feel confining to many patients. Furthermore, Fourier transform techniques may be used to facilitate image reconstruction, at the cost of constraints on the RF pulse sequences and, thus, the MR scan time.

The combination of long MR scan times and, in the case of MRI, the confining environment of the magnet bore can degrade the user experience. In addition, long MR scan times reduce throughput, thereby increasing the cost of performing the characterization. These types of problems can constrain or limit the use of many characterization techniques.

Additionally, it can be difficult to perform longitudinal analysis or tracking using many characterization techniques. For example, longitudinal tracking using MRI requires repetitive scans of an individual as a function of time. However, MRI was originally designed as a qualitative characterization technique that was optimized for acute diagnostics. MRI was not designed to measure or quantify longitudinal changes accurately in anatomical structures or tissue properties. Some existing approaches attempt to accelerate longitudinal analysis of MRI scans with historical information. These existing approaches typically require a pixel-wise registration and often fail to capture new or changed anatomical features.

SUMMARY

A computer system that performs a sparsity technique is described. This computer system (which includes one or more computers) includes: an interface circuit that communicates, e.g., with a measurement device (which performs measurements), a processor that executes program instructions, and memory that stores the program instructions. During operation, the computer system accesses or obtains information associated with non-invasive measurements performed on at least an individual, historical non-invasive measurements, and a dictionary of predetermined features or basis functions associated with the historical non-invasive measurements. Then, the computer system updates the dictionary of predetermined features based at least in part on the non-invasive measurements and the historical non-invasive measurements, where the updating includes performing a minimization technique with a cost function having an L2-norm term and an L0-norm term. Next, the computer system determines weights associated with features in the updated dictionary of predetermined features based at least in part on the non-invasive measurements.

Note that the non-invasive measurements and the historical non-invasive measurements may include or correspond to MR measurements. For example, the MR measurements may include MRI scans.

Moreover, the non-invasive measurements and the historical non-invasive measurements may include MR parameters associated with voxels in the individual. For example, the parameters may include: a density of a type of nuclei, a longitudinal relaxation time along a direction parallel to an external magnetic field and/or a transverse relaxation time along a direction perpendicular to the external magnetic field.

Furthermore, the non-invasive measurement may include at least a component of a magnetization associated with the individual, and the computer system may: calculate at least a predicted component of the magnetization for the voxels associated with the individual based at least in part on the measured component of the magnetization, a forward model, an external magnetic field and an RF pulse sequence; and solve an inverse problem by iteratively modifying the parameters associated with the voxels in the forward model until a difference between the predicted component of the magnetization and the measured component of the magnetization is less than a predefined value.

Additionally, the historical non-invasive measurements may be associated with the individual or a group of individuals. In some embodiments, the group of individuals may exclude the individual.

Note that determining the weights may include a gradient-descent technique.

Moreover, the dictionary of predetermined features and the updated dictionary of predetermined features may correspond to a portion of an anatomy of the individual.

Another embodiment provides a computer-readable storage medium for use with the computer system. This computer-readable storage medium includes program instructions that, when executed by the computer system, causes the computer system to perform at least some of the aforementioned operations.

Another embodiment provides a method for performing a sparsity technique. This method includes at least some of the aforementioned operations performed by the computer system.

This Summary is provided for purposes of illustrating some exemplary embodiments, so as to provide a basic understanding of some aspects of the subject matter described herein. Accordingly, it will be appreciated that the above-described features are simply examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
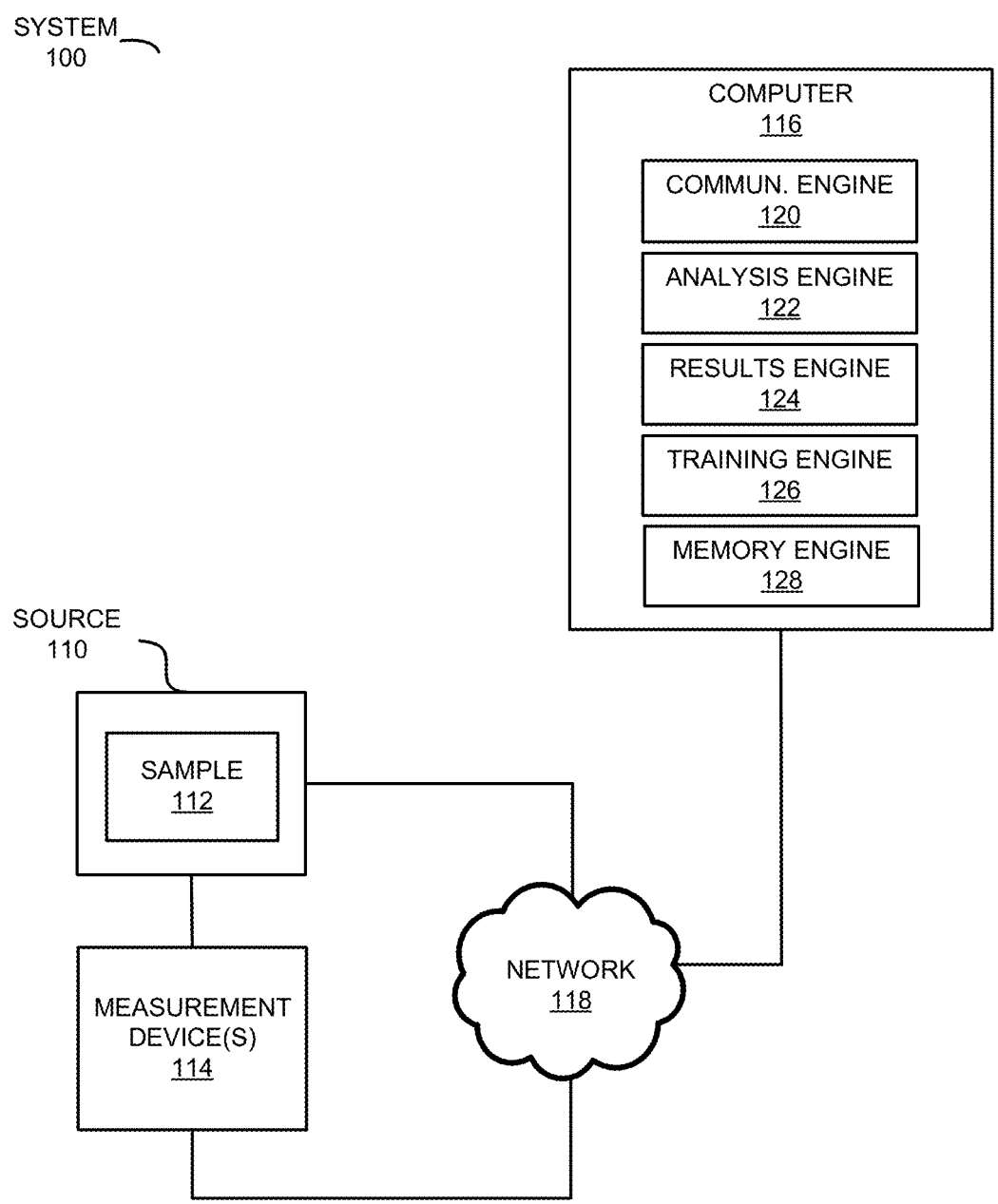
FIG. 1 is a block diagram illustrating an example of a system in accordance with an embodiment of the present disclosure.

In a first group of embodiments, a computer system that performs a sparsity technique is described. During operation, the computer system accesses or obtains information associated with non-invasive measurements performed on at least an individual, historical non-invasive measurements (associated with the individual or a group of individuals), and a dictionary of predetermined features or basis functions associated with the historical non-invasive measurements (and which corresponds to at least a portion of the anatomy of the individual or the group of individuals). Note that the non-invasive measurements and the historical non-invasive measurements may include or correspond to MR measurements. For example, the MR measurements may include MRI scans. Then, the computer system updates the dictionary of predetermined features based at least in part on the non-invasive measurements and the historical non-invasive measurements, where the updating includes performing a minimization technique with a cost function having an L2-norm term and an L0-norm term. Next, the computer system determines weights associated with features in the updated dictionary of predetermined features based at least in part on the non-invasive measurements.

By updating the dictionary of predetermined features and determining the weights, these analysis techniques may facilitate quantitative analysis of the non-invasive measurements. For example, the analysis techniques may allow quantitative longitudinal analysis to be performed on MR scans. This longitudinal analysis may not require pixel-level registration of the MR scans. Moreover, because the analysis techniques provide a sparse representation of the MR scans, the comparisons during the longitudinal analysis may be performed more efficiently and accurately, which may allow new or modified anatomical features to be captured. In addition, the sparse representation may allow subsequent MR scans to be performed differentially (such as an MR scan of one or more regions with changes relative to the historical non-invasive measurements) and, thus, more rapidly. Consequently, the analysis techniques may facilitate more accurate analysis of MR scans, may reduce the time and cost of performing an MR scan, and may improve the overall user experience.

In a second group of embodiments, a computer system (including one or more computers) that determines coefficients in a representation of coil sensitivities and MR information associated with a sample is described. During operation, the computer system may acquire MR signals associated with a sample from the measurement device. Then, the computer system may access a predetermined set of coil magnetic field basis vectors, where weighted superpositions of the predetermined set of coil magnetic field basis vectors using the coefficients represent coil sensitivities of coils in the measurement device, and where the predetermined coil magnetic field basis vectors are solutions to Maxwell's equations. Next, the computer system may solve a nonlinear optimization problem for the MR information associated with the sample and the coefficients using the MR signals and the predetermined set of coil magnetic field basis vectors.

By representing the coil sensitivities and solving the nonlinear optimization problem, this computation technique may reduce an MR scan time for measuring the MR signals. For example, the operations performed by the computer system may allow multiple MR scan lines in measurements made by the measurement device to be skipped and subsequently reconstructed when solving the nonlinear optimization technique. Separately or in addition to a reduction in the time needed to solve the nonlinear optimization problem, this capability may reduce an MR scan time associated with the measurements performed by the measurement device. Indeed, the computation technique may achieve a theoretical limit for the possible acceleration in the MR scan time for a given set of coils, a field-of-view, an external magnetic field strength (or resolution), and for a 2D or a 3D measurement. Consequently, the computation technique may reduce the cost of performing an MR scan and may improve the overall user experience.

In a third group of embodiments, as discussed previously, existing MRI approaches often have a large number of MR scans and long MR scan times, as well as expensive magnets and/or a confining environment of the magnet bore, which can degrade the user experience.

One approach for addressing these problems is to use simulations of the response physics of a sample to one or more excitations to determine information, such as the one or more physical parameters. For example, using model parameters at the voxel level and a forward model based on one or more differential equations that describe a physical phenomenon, a computer system can simulate the response physics of the sample as an output of the forward model using information specifying the one or more excitations as an input to the forward model.

However, this approach often replaces the problems of having a large number of MR scans and long MR scan times, with the problems associated with accurately determining the model parameters at the voxel level. For example, the model parameters are typically determined by iteratively applying one or more excitations, performing measurements and then solving an inverse problem of using the measurements to compute the corresponding model parameters until a desired accuracy of the simulated response physics is achieved (which is sometimes referred to as an 'iterative approach'). In general, it can be difficult, time-consuming and expensive to determine the model parameters using these existing techniques, which may constrain or limit the use of simulations of the response physics to characterize a sample.

In the third group of embodiments, a system that determines model parameters associated with a sample is described. During operation, the system may apply, to the sample, the excitation using the source. Then, the system may measure, using a measurement device, a response associated with the sample to the excitation. Moreover, the system may compute, using the measured response and information specifying the excitation as inputs to a predetermined predictive model, model parameters on a voxel-by-voxel basis in a forward model with multiple voxels that represent the sample. The forward model may simulate response physics occurring within the sample to a given excitation. Furthermore, the forward model may be a function of the excitation, the model parameters of the multiple voxels, and differential or phenomenological equations that approximates the response physics. Next, the system may determine, using the processor, an accuracy of the model parameters by comparing at least the measured response and a calculated predicted value of the response using the forward model, the model parameters and the excitation. Additionally, when the accuracy exceeds a predefined value, the system may provide the model parameters as an output to a user, to another electronic device, to a display and/or to a memory.

By determining the model parameters for voxels in the sample (which is sometimes referred to as 'tensor field mapping' or TFM, because the parameters in the voxels can be represented by a hybrid tensor as opposed to a true tensor for a vector field), this computation technique may reduce or eliminate the need for iterative measurements and adaptation when determining the model parameters. Consequently, the computation technique may significantly reduce the use of system resources (such as processor time, memory, etc.) when determining the model parameters. Moreover, if the accuracy is insufficient (such as when the accuracy is less than the predefined value), the computation technique may be used to guide a modification to the excitation to facilitate rapid convergence on the model parameters with the desired accuracy. Furthermore, by providing a forward model that predicts a physical phenomenon based on the determined model parameters for a range of excitation values or intensities, the computation technique may facilitate rapid and accurate characterization of a sample (such as the determination or one or more physical parameters of a sample). Therefore, the computation technique can be used to dynamically adapt or modify the excitation used in the measurements and/or may facilitate improved sample characterization.

These capabilities may result in shorter MR scan or measurement times, increased throughput and, thus, reduced measurement cost, an improved user experience (such as by reducing the amount of time people spend in the confining environment of a magnet bore in an MR scanner), and increased use of characterization techniques. In addition, the computation technique may facilitate quantitative analysis of measurements, which may improve the accuracy, may reduce errors and, thus, may improve the health and well-being of people.

In general, the computation technique may be used in conjunction with a variety of characterization techniques and forward models that quantitatively simulate the response physics occurring within the sample to a given excitation. For example, the characterization technique may involve: x-ray measurements (such as x-ray imaging, x-ray diffraction or computed tomography), neutron measurements (neutron diffraction), electron measurements (such as electron microscopy or electron spin resonance), optical measurements (such as optical imaging or optical spectroscopy that determines a complex index of refraction at one or more wavelengths), infrared measurements (such as infrared imaging or infrared spectroscopy that determines a complex index of refraction at one or more wavelengths), ultrasound measurements (such as ultrasound imaging), proton measurements (such as proton scattering), MR measurements or an MR technique (such as MRI, MR spectroscopy or MRS with one or more types of nuclei, magnetic resonance spectral imaging or MRSI, MR elastography or MRE, MR thermometry or MRT, magnetic-field relaxometry, diffusion-tensor imaging and/or another MR technique, e.g., functional MRI, metabolic imaging, molecular imaging, blood-flow imaging, etc.), impedance measurements (such as electrical impedance at DC and/or an AC frequency) and/or susceptibility measurements (such as magnetic susceptibility at DC and/or an AC frequency). Therefore, the excitation may include at least one of: an electromagnetic beam in an x-ray band of wavelengths (such as between 0.01 and 10 nm), a neutron beam, an electron beam, an electromagnetic beam in an optical band of wavelengths (such as between 300 and 800 nm), an electromagnetic beam in an infrared band of wavelengths (such as between 700 nm and 1 mm), a sound wave in an ultrasound band of wavelengths (such as between 0.2 and 1.9 mm), a proton beam, an electric field associated with an impedance measurement device, a radio-frequency wave associated with an MR apparatus or scanner, and/or a magnetic field associated with a susceptibility measurement device. However, another non-invasive characterization technique (such as positron emission spectroscopy), an integrated therapy (such as proton beam therapy or proton implantation, radiation therapy, magnetically guided nano particles, etc.) and/or a different range of wavelengths (such as ultraviolet wavelengths between 10 and 400 nm) may be used. In general, the computation technique may be used with a wide variety of excitation may be used to 'excite' a region of space as long as there is a forward model that describes the response physics for these excitations. In the discussion that follows, an MR technique is used as an illustrative example of a characterization technique.

Note that the sample may include an organic material or an inorganic material. For example, the sample may include: an inanimate (i.e., non-biological) sample, a biological lifeform (such as a person or an animal, i.e., an in-vivo sample), or a tissue sample from an animal or a person (i.e., a portion of the animal or the person). In some embodiments, the tissue sample was previously removed from the animal or the person. Therefore, the tissue sample may be a pathology sample (such as a biopsy sample), which may be formalin fixed-paraffin embedded. In the discussion that follows, the sample is a person or an individual, which is used as an illustrative example.

We now describe embodiments of a system. FIG. 1 presents a block diagram illustrating an example of a system 100. In system 100, a source 110 selectively provides an excitation to a sample 112, and a measurement device 114 selectively performs measurements on sample 112 to measure a response of sample 112 to the excitation. Moreover, system 100 includes a computer 116. As described further below with reference to FIG. 16, computer 116 may include subsystems, such as a processing subsystem, a memory subsystem and a networking subsystem. For example, the processing subsystem may include a processor that executes program instructions, the memory subsystem may include a memory that stores the program instructions, and networking subsystem may include an interface that communicates instructions or commands to source 110 and measurement device 114 (such as one or more sensors), that receives measurements from measurement device 114, and that selectively provides determined model parameters.

During operation, a communication engine (or module) 120 in computer 116 may provide, via a network 118 (such as one or more wired and/or wireless links or interconnects), an instruction or a command to source 110, which may cause source 110 to apply, to sample 112, the excitation. This excitation may have at least a wavelength and an intensity or a flux. For example, the excitation may include: electromagnetic radiation, a radio-frequency wave, a particle beam, a sound wave, a magnetic field, and/or an electric field.

In some embodiments, the excitation may include an external magnetic field that polarizes one or more types of nuclei in sample 112, an optional gradient in the magnetic field, and/or an RF pulse sequence (which are sometimes referred to as 'measurement conditions' or 'scanning instructions'). Thus, source 110 may include a magnet that applies the external magnetic field, an optional gradient coil that applies the optional gradient, and/or an RF coil that applies the RF pulse sequence.

Then, communication engine 120 may provide, via network 118, an instruction or a command to measurement device 114, which may cause measurement device 114 to perform measurements of the response of at least a portion of sample 112 to the excitation. Moreover, measurement device 114 may provide, via network 118, the measurement results to communication engine 120. Note that measurement device 114 may include: an x-ray detector, a neutron detector, an electron detector, an optical detector, an infrared detector, an ultrasound detector, a proton detector, an MR apparatus or scanner, the impedance measurement device (such as a gel-covered table in an MR apparatus or scanner) and/or the susceptibility measurement device.

In some embodiments, measurement device 114 may include one or more RF pickup coils or another magnetic sensor (such as a magnetometer, a superconducting quantum interference device, opto-electronics, etc.) that measure time-varying or time-domain electrical signals corresponding to the dynamic behavior of nuclear spins in the one or more types of nuclei or at least an average component of the magnetization corresponding to the aggregate dynamic behavior of the nuclear spins (which is sometimes referred to as a 'magnetic response') of at least the portion of sample 112. For example, measurement device 114 may measure the transverse magnetization of at least a portion of sample 112 as it precesses in the xy plane.

Note that the measurements provided by measurement device 114 may be other than or different from an image. For example, the measurements may be other than MRI results. For example, the measurements may include or may correspond to (such as one or more components of) a free-induction-decay of the nuclear spins in sample 112. Consequently, in some embodiments the measurements may not involve performing a Fourier transform on the measured electrical signals (and, thus, may not be performed in k-space and may not involve pattern matching in k-space, such as MR fingerprinting). However, in general, the measurements may be specified in the time domain and/or the frequency domain. Therefore, in some embodiments, a variety of signal processing (such as filtering, image processing, etc.), noise cancellation and transformation techniques (such as a discrete Fourier transform, a Z transform, a discrete cosine transform, data compression, etc.) may be performed on the measurements.

After receiving the measurements, analysis engine (or module) 122 in computer 116 may analyze the measurements. This analysis may involve determining a (possibly time-varying) 3D position of sample 112 relative to measurement device 114 (which is sometimes referred to as '3D registration information'). For example, the aligning may involve performing point-set registration, such as with reference markers at known spatial locations. The registration may use a global or a local positioning system to determine changes in the position of sample 112 relative to measurement device 114. Alternatively or additionally, the registration may be based at least in part on variation in the Larmor frequency and the predetermined spatial magnetic-field inhomogeneity or variation in the magnetic field of source 110 and/or measurement device 114 (such as an MR apparatus or scanner). In some embodiments, the analysis involves aligning the voxels based at least in part on the registration information with desired voxel locations, and/or resampling and/or interpolating the measured signals to different voxel locations, which may facilitate subsequent comparisons with previous measurements or results.

Moreover, analysis engine 122 may use the measurements to determine model parameters for a forward model with multiple voxels that represent sample 112, and that simulates the response physics occurring in sample 112 to a given excitation in a range of possible excitations (i.e., the forward model may be more general than one that determines the predicted response to a particular or a specific excitation). Notably, with the appropriate model parameters for the voxels in sample 112, analysis engine 122 may use the forward model to accurately and quantitatively simulate or calculate a predicted response of sample 112 to the excitation (such as a predicted component of the magnetization). Note that the forward model may be based at least in part on or may use one or more differential equations or one or more phenomenological equations that approximates the response physics of sample 112 on a voxel-by-voxel basis. For example, the forward model may be based at least in part on or may use the Bloch equations, the Bloch-Torrey equations (thus, the forward model may include simulations of dynamics, such as motion associated with: respiration, a heartbeat, blood flow, mechanical motion, etc.), full Liouvillian computations (such as a Liouville supermatrix of interactions between two or more elements), a full Hamiltonian, Maxwell's equations (e.g., the forward model may calculate magnetic and electrical properties of sample 112), thermal diffusion equations, the Pennes equations, and/or another simulation technique that represents the physics of a response of sample 112 to a type of excitation. Because in some embodiments the assumptions underlying the Bloch equations are invalid (such as the parallel and antiparallel components of the magnetization are coupled, e.g., when the state of the magnetization is not reset prior to an RF pulse sequence), additional error terms may be added to the Bloch equations. Therefore, the forward model may be able to compute a dynamic (e.g., time-varying) state of sample 112 in response to an arbitrary excitation in a range of possible excitations or excitation values.

In some analysis approaches, computer 116 may determine the model parameters by solving an inverse problem by iteratively modifying the model parameters associated with the voxels in the forward model until a difference between the predicted response and the measured dynamic magnetic response is less than a predefined value (such as 0.1, 1, 5 or 10%). (Note that 'an inverse problem' starts with one or more result(s) or output(s) and then calculates the inputs or causes. This is the inverse of a 'forward problem,' which starts with the inputs and then calculates the one or more results or the outputs.) However, in this 'iterative approach,' source 110 may repeatedly apply different excitations, and measurement device 114 may repeatedly perform corresponding measurements. Consequently, the iterative approach may be time-consuming, expensive and complicated. Thus, the iterative approach may consume significant resources in system 100 until the appropriate model parameters are determined.

As described further below with reference to FIGS. 2-5, in order to address these problems, in the computation technique analysis engine 122 may use one or more predetermined or pretrained predictive models (such as a machine-learning model or a neural network, which may be specific to a particular sample or an individual, e.g., the predictive model may be a personalized predictive model) to, at least in part, compute the model parameters on a voxel-by-voxel basis. For example, analysis engine 122 may use the measurements and information specifying the excitation as inputs to a predictive model, which provides, as an output, the model parameters associated with the voxels. Therefore, the predictive model may be trained on or may incorporate model-parameter information based at least in part on measurements or measurement results. In some embodiments, the predictive model may correct the measurements for extrinsic characteristics or a signature of a specific source 110 and/or measurement device 114 (such as RF noise or spatial magnetic-field inhomogeneity) and/or a particular excitation or measurement condition, so that the determined model parameters are intrinsic to sample 112 at a particular time when the measurements were performed.

Note that the model parameters may include: a spin-lattice relaxation time $T_1$ (which is the time constant associated with the loss of signal intensity as components of the nuclear-spin magnetization vector of a type of nuclei relax to be parallel with the direction of an external magnetic field), a spin-spin relaxation time $T_2$ (which is the time constant associated with broadening of the signal during relaxation of components of the nuclear-spin magnetization vector of a type of nuclei perpendicular to the direction of the external magnetic field), an adjusted spin-spin relaxation time $T_2^*$, proton or nuclei density (and, more generally, the densities of one or more type of nuclei), diffusion (such as components in a diffusion tensor), velocity/flow, temperature, off-resonance frequency, electrical conductivity or a dielectric constant, and/or a magnetic susceptibility or permittivity.

If a subsequent simulation using these model parameters provided by the predictive model, the forward model and one or more excitations of one or more predicted responses of sample 112 (such as a simulated or predicted MR signal) agrees with the corresponding measurements (such as a difference between a predicted response and a measurement is less than a predefined value, e.g., 0.1, 1, 5 or 10%, or alternatively when an accuracy exceeds a predefined value), results engine (or module) 124 in computer 116 may provide the determined model parameters, such as by providing an output to a user, to another electronic device, to a display and/or to the memory. In some embodiments, results engine 124 may output a tensor field map for sample 112 with model parameters for 3 spatial x one temporal x up to N measurement dimensions, where each measurement may be a vector or scalar quantity.

Thus, when the accuracy exceeds the predefined value (such as 90, 95, 99 or 99.9%), the model parameters may be computed in a single pass without further iteration. Consequently, the model parameters having an accuracy exceeding the predefined value may be computed using fewer (or no) iterations with the predetermined predictive model (and, thus, more rapidly) than in the iterative approach without the predetermined predictive model.

Alternatively, when the accuracy is less than the predefined value, computer 116 may perform one or more iterations in which one or more different, modified or revised excitations (such as a different RF pulse sequence) are applied to sample 112 by source 114, and one or more corresponding additional measurements are performed by measurement device 114. These one or more additional measurements may be used by computer 116 to determine the model parameters with an accuracy less than the predefined value.

For example, analysis engine 122 may use a second predetermined predictive model (such as a second machine-learning model or a second neural network) to determine a revised excitation. Notably, using information specifying the excitation and the accuracy as inputs, the second predictive model may output the revised excitation. Then, system 100 may repeat the applying, measuring, computing and determining operations with the revised excitation instead of the excitation. Therefore, the second predictive model may be trained on or may incorporate excitation information based at least in part on remaining differences between the predicted response and the measurement in order to reduce or eliminate the remaining differences in one or more subsequent iterations of the operations performed by system 100. In some embodiments, the second predictive model may revise a sampling frequency, a characterization technique, etc. to determine additional information that allows the determination of the model parameters using the first predictive model to converge (i.e., to have an accuracy less than the predefined value). Stated differently, the next perturbation or disturbance may be chosen to minimize the error or the difference across the hyper-dimensional space.

In some embodiments, when the accuracy is less than the predefined value, training engine (or module) 126 in computer 116 may: add the excitation and the measured response to a training dataset; and determine, using the training dataset, a revised instance of the predictive model for subsequent use in determining the model parameters. Thus, the measurements performed by system 100 may be selectively used in an adaptive learning technique to improve the predictive model and, therefore, the determined model parameters for a range of excitations (such as different values of the wavelength and the intensity or the flux).

Using the model parameters and the forward model, analysis engine 122 may simulate or predict a response of sample 112 to an arbitrary excitation, such as an arbitrary external magnetic field strength or direction (such as 0 T, 6.5 mT, 1.5 T, 3 T, 4.7 T, 9.4 T, and/or 15 T, or a time-varying direction, e.g., a slowly rotating external magnetic field), an arbitrary optional gradient, an arbitrary pulse sequence, an arbitrary magnetic state or condition (e.g., in which the magnetization or polarization of sample 112 is not returned to, been reset to or re-magnetized to an initial state prior to a measurement), etc. Therefore, the model parameters and the forward model may be used to facilitate fast and more accurate measurements, such as: soft-tissue measurements, morphological studies, chemical-shift measurements, magnetization-transfer measurements, MRS, measurements of one or more types of nuclei, Overhauser measurements, and/or functional imaging. For example, in embodiments where computer 116 determines the model parameters concurrently with measurements performed on sample 112 by source 110 and measurement device 114 (i.e., in real time), system 100 may rapidly characterize one or more physical parameters of sample 112 (at the voxel level or on average) on time scales smaller than $T_1$ or $T_2$ in an arbitrary type of tissue. This capability may allow system 100 to perform initial measurements to determine the model parameters, and then to use the determined model parameters to simulate or predict MR signals to complete or fill in ongoing measurements being performed by system 100, so that the results can be obtained more rapidly (and, thus, with a shorter MR scan time). Note that, in some embodiments, system 100 may determine the results (such as detecting an anomaly or a change in sample 112) based at least in part on quantitative comparisons of previous results obtained on sample 112, such as stored model parameters for the voxels in sample 112 that were determined during a previous MR scan(s) of sample 112. Such comparisons may be facilitated by 3D registration information that allows the voxel positions in sample 112 at different times to be aligned. In some embodiments, the results are based at least in part on a physician's instructions, medical lab test results (e.g., a blood test, urine-sample testing, biopsies, genetic or genomic testing, etc.), an individual's medical history, the individual's family history, quantitative tensor field maps with voxel-dependent multi-dimensional data for sample 112 or other samples, impedance of sample 112, a hydration level of sample 112 and/or other inputs.

Furthermore, as described further below with reference to FIG. 6, in some embodiments analysis engine 122 may classify or segment one or more anatomical structures in sample 112 using the determined model parameters and a third predetermined predictive model (such as a third machine-learning model and/or a third neural network). For example, using the simulated or predicted response of sample 112 at the voxel level or the determined model parameters at the voxel level, the third predictive model may output the locations of different anatomical structures and/or may output classifications of different voxels (such as a type of organ, whether they are associated with a particular disease state, e.g., a type of cancer, a stage of cancer, etc.). Therefore, in some embodiments, the third predictive model may be trained on or may incorporate classification of segmentation information based at least in part on variation in the model parameters across boundaries between different voxels (such as discontinuous changes). This capability may allow analysis engine 122 to identify different anatomical structures (which may assist in the determination of the model parameters) and/or to diagnose or to make a diagnosis recommendation about a medical condition or a disease state. In some embodiments, the classification or segmentation is performed prior to, concurrently or following the determination of the model parameters.

In some embodiments, training engine 126 may have, at least in part, trained the predictive model, the second predictive model and/or the third predictive model using a simulated dataset. For example, training engine 126 may have generated the simulated dataset using the forward model, a range of model parameters and a range of excitations. In this way, simulated data may be used to accelerate training of one or more predictive models.

Notably, because the computation technique may capture all relevant information during the measurements (such as an MR scan), the forward model can be used in an off-line mode to curate an extensive, labeled dataset that includes a large number of possible scenarios (such as different measurement conditions). This database can then be used to train predictive models. This capability may address the difficulty in obtaining MR data that is accurately labeled, reproducible, and artifact-free.

In conjunction with the generated dataset, one or more predictive models can be used to select regularization that accelerates the initial data acquisition and/or denoising. Moreover, the one or more predictive models can also be used to accelerate simulations or reconstruction using the forward model. For example, a predictive model can provide initial model parameters for use in the forward model, which may reduce the number of iterations required for the measurements and the simulations to converge on a solution that has an accuracy exceeding the predefined value. Thus, if the initial model parameters result in predicted response that are very different from the measurements, this can be feedback into the subsequent measurements and simulations to improve the model parameters and, thus, the predicted response.

Furthermore, if there is a portion of the model-parameter space that is not covered by the predictive model(s), new data points can be accurately generated and labeled to train the predictive model(s). Additionally, the predictive model(s) may be trained based on different metrics corresponding to different applications. For example, the predictive model(s) may be training to optimize the excitations used in difference scenarios (such as fast scanning for asymptomatic population, high accuracy for specific tissue properties, robustness to variations in the signal-to-noise ratio, different hardware imperfections, etc.).

In some embodiments, analysis engine 122 may run a neural network that determines first model parameters based at least in part on measured or simulated data and may performs brute-force nonlinear numerical calculations to solve an inverse problem using the measured or the simulated data to determine second model parameters. The difference between the first and the second model parameters from these two 'inverse solvers' may be used as the error in the neural-network-based approach. This approach may allow the neural network to learn because the numerical approach may be able to give real-time feedback to the neural network and to back propagate/update the weights in the neural network. This hybrid approach would still not require or need a priori training, but would be able to leverage the pattern-matching benefits of large neural networks with the determinism and accuracy of simulation/numerical techniques to solve the inverse problem. The hybrid approach may assist the neural network when it has an input unlike any of the examples used to train it. Similarly, the hybrid approach may be used to go directly from time-domain measurement to the model-parameterized output (i.e. the inverse problem outputs). In some embodiments, the hybrid approach is implemented using a generative adversarial network (GAN).

Note that, in some embodiments, the forward model may be independent of a particular MR apparatus or scanner. Instead, the forward model may be, e.g., specific to an individual. The predicted response computed using the forward model may be adjusted to include characteristics or a signature of a particular MR apparatus or scanner, such as magnetic-field inhomogeneity or spatial variation in the magnetic field, RF noise, a particular RF pickup coil or another magnetic sensor, variation in the characteristics or the signature with the external magnetic-field strength or the measurement conditions (such as the voxel size), geographic location, time (due to, e.g., magnetic storms), etc. Thus, the predicted response may be machine-specific.

While the preceding discussion illustrated the computation technique using a single predictive model for sample 112, in other embodiments there may be multiple predictive models for sample 112. For example, different predictive models may be used to determine the model parameters for different portions of sample 112 (such as different organs or different types of tissue) and, thus, for different voxels. Therefore, in some embodiments different predictive models may be used to provide $T_1$ and $T_2$ values in different types of tissue, such as the values summarized in Table 1.

TABLE 1

| Tissue | $T_1$ (s) | $T_2$ (ms) |
| --- | --- | --- |
| Cerebrospinal Fluid | 0.8-20 | 110-2000 |
| White Matter | 0.76-1.08 | 61-100 |
| Gray Matter | 1.09-2.15 | 61-109 |
| Meninges | 0.5-2.2 | 50-165 |
| Muscle | 0.95-1.82 | 20-67 |
| Adipose | 0.2-0.75 | 53-94 |

Additionally, as described further below with reference to FIGS. 9-15, in some embodiments, analysis engine 122 may receive information associated with or specifying results of measurements (which are sometimes referred to as non-invasive measurements) performed on an individual from measurement device 114 or may access or obtain the information in local or remote memory in or associated with system 100 via memory engine 128 (or module). Moreover, analysis engine 122 may access or obtain, via memory engine 128, historical non-invasive measurements (which were performed on the individual or a group of individuals, and which may include or may exclude the individual) and a dictionary of predetermined features or basis functions associated with the historical non-invasive measurements.

Note that the non-invasive measurements and the historical non-invasive measurements may include or correspond to MR measurements. For example, the MR measurements may include MRI scans. Moreover, the non-invasive measurements and the historical non-invasive measurements may include MR parameters associated with voxels in the individual. Notably, the parameters may include: a density of a type of nuclei, a longitudinal relaxation time along a direction parallel to an external magnetic field and/or a transverse relaxation time along a direction perpendicular to the external magnetic field.

Then, analysis engine 128 may update the dictionary of predetermined features based at least in part on the non-invasive measurements and the historical non-invasive measurements. Notably, the updating may include performing a minimization technique with a cost or error function having an L2-norm term and an L0-norm term. Next, analysis engine 128 may determine (e.g., using a gradient-descent technique) weights associated with features in the updated dictionary of predetermined features (such as weights in a weighted linear superposition of the features in the updated dictionary) based at least in part on the non-invasive measurements. For example, the weights may be determined by performing a least-squares fit of the non-invasive measurements based at least in part on the features in the updated dictionary and/or by using the gradient-descent technique. In some embodiments, the weights may be determined using a pretrained machine-learning model (such as a supervised-learning model or a neural network) that outputs the weights based at least in part on the in the updated dictionary of predetermined features and the non-invasive measurements. In conjunction with the features in the updated dictionary, the weights may provide a sparse representation of the non-invasive measurements. Note that the dictionary of predetermined features and the updated dictionary of predetermined features may correspond to a portion of an anatomy of the individual.

Furthermore, results engine 124 may present or provide the sparse representation, such as by providing an output to a user, to another electronic device, to a display and/or to the memory (via memory engine 128).

In some embodiments, analysis engine 122 may perform analysis on the sparse representation of the non-invasive measurements. For example, the non-invasive measurement may include at least a component of a magnetization associated with the individual, and analysis engine 122 may: calculate at least a predicted component of the magnetization for the voxels associated with the individual based at least in part on the measured component of the magnetization, a forward model, the external magnetic field and an RF pulse sequence used to measure the non-invasive measurement; and solve an inverse problem by iteratively modifying the parameters associated with the voxels in the forward model until a difference between the predicted component of the magnetization and the measured component of the magnetization is less than a predefined value (such as a difference or error of 1, 5 or 10%).

Alternatively or additionally, analysis engine 122 may perform a longitudinal analysis of the non-invasive measurements based at least in part on the sparse representation and sparse representations of at least a subset of the historical non-invasive measurements. Note that the longitudinal analysis may not require or use a pixel-level registration operation between the non-invasive measurements and the subset of the historical non-invasive measurements. Moreover, by using the prior information, the longitudinal analysis may be used to detect changes, e.g., in an anatomical feature and, more generally, in the non-invasive measurements relative to a baseline provided by at least the subset of the historical non-invasive measurements. Thus, if it is known that an individual is at risk for liver cancer, more time may be spent acquiring high-quality images of their liver. Based at least in part on the detected changes, communication engine 116 may provide instructions to source 110 and/or measurement device 114 to perform an additional non-invasive measurement of at least a portion of the individual associated with the change. Results engine 124 may present or provide results of the longitudinal analysis (e.g., information specifying the detected change), such as by providing an output to the user, to another electronic device, to the display and/or to the memory (via memory engine 128).

Moreover, while system 100 is illustrated as having particular components, in other embodiments system 100 may have fewer or more components, two or more components may be combined into a single component, and/or positions of one or more components may be changed.

Figure 2:
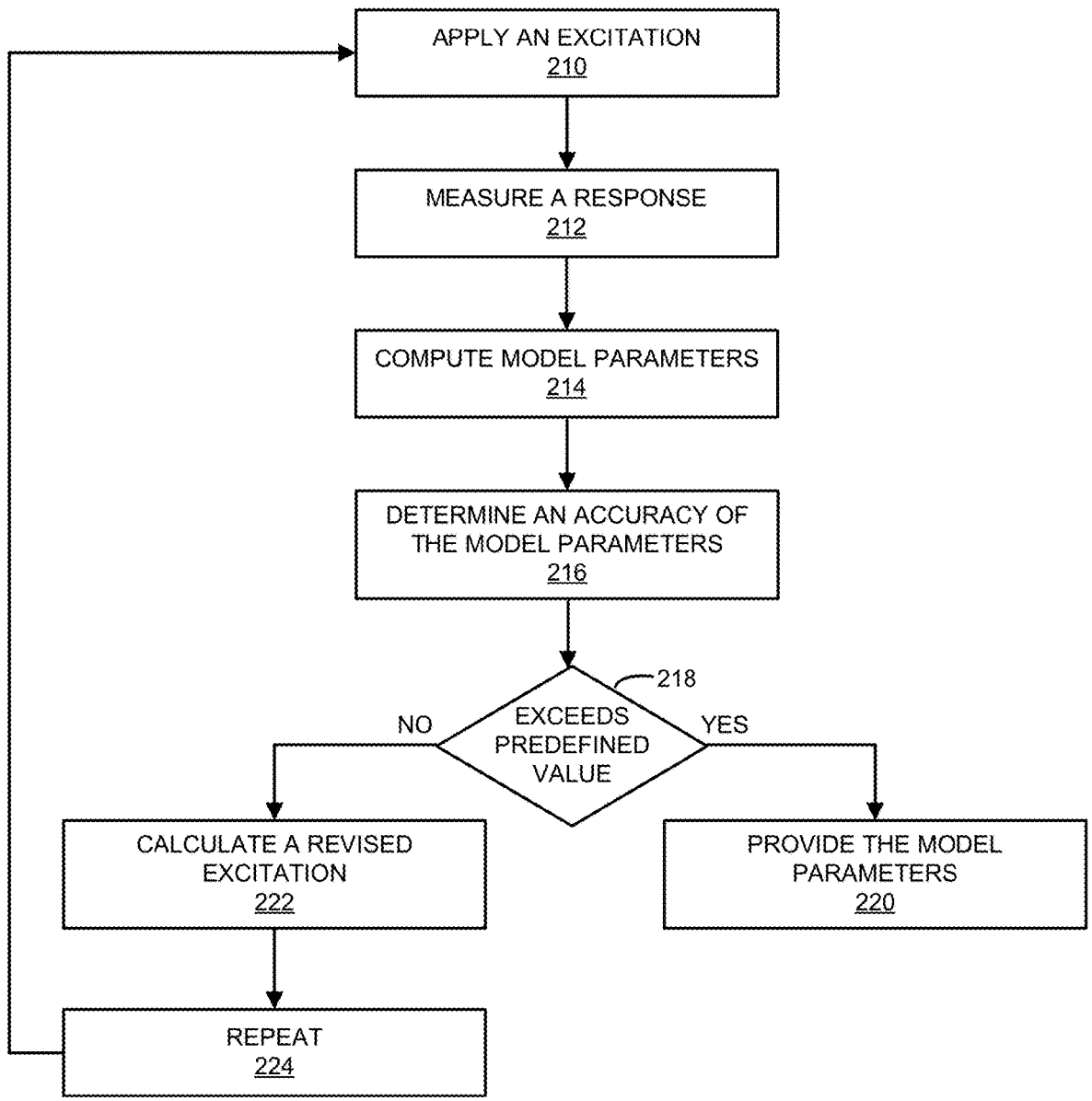
FIG. 2 is a flow diagram illustrating an example of a method for determining model parameters associated with a sample in accordance with an embodiment of the present disclosure.

We now describe embodiments of a method. FIG. 2 presents a flow diagram illustrating an example of a method 200 for determining model parameters associated with a sample. This method may be performed by a system (such as system 100 in FIG. 1), or one or more components in a system (such as source 110, measurement device 114 and/or computer 116).

During operation, a source in the system may apply, to the sample, an excitation (operation 210), where the excitation has at least a wavelength and an intensity or a flux. For example, the excitation may include one of: electromagnetic radiation, a radio-frequency wave, a particle beam, a sound wave, a magnetic field, and/or an electric field. Therefore, the excitation may include at least one of: an electromagnetic beam in an x-ray band of wavelengths, a neutron beam, an electron beam, an electromagnetic beam in an optical band of wavelengths, an electromagnetic beam in an infrared band of wavelengths, a sound wave in an ultrasound band of wavelengths, a proton beam, an electric field associated with an impedance measurement device, a radio-frequency wave associated with a magnetic-resonance apparatus, and/or a magnetic field associated with a susceptibility measurement device.

Then, a measurement device in the system may measure a response (operation 212) associated with the sample to the excitation. For example, the measurement device may include at least one of: an x-ray detector, a neutron detector, an electron detector, an optical detector, an infrared detector, an ultrasound detector, a proton detector, the magnetic-resonance apparatus, the impedance measurement device and/or the susceptibility measurement device. Note that the measured response may include a time-domain response of the sample and may be other than or different from an image.

Moreover, the system may compute, using the measured response and information specifying the excitation as inputs to a predetermined predictive model, model parameters (operation 214) on a voxel-by-voxel basis in a forward model with multiple voxels that represent the sample. The forward model may simulate response physics occurring within the sample to a given excitation with a given wavelength and a given intensity or a given flux, that are selected from a range of measurement conditions that includes the excitation, the wavelength and the intensity or the flux, and at least a different wavelength and a at least a different intensity or a different flux. Furthermore, the forward model may be a function of the excitation, the model parameters of the multiple voxels, and differential or phenomenological equations that approximates the response physics.

Note that the predetermined predictive model may include a machine-learning model and/or a neural network. In some embodiments, the predetermined predictive model includes a personalized predictive model that corresponds to an individual.

Next, the system may determine an accuracy of the model parameters (operation 216) by comparing at least the measured response and a calculated predicted value of the response using the forward model, the model parameters and the excitation.

Additionally, when the accuracy exceeds a predefined value (operation 218), the system may provide the model parameters (operation 220) as, e.g., an output to a user, to another electronic device, to a display and/or to the memory.

Thus, when the accuracy exceeds the predefined value (operation 218), the model parameters may be computed in a single pass without further iteration. Consequently, the model parameters having an accuracy exceeding the predefined value may be computed using fewer iterations with the predetermined predictive model than in the iterative approach without the predetermined predictive model.

Alternatively, when the accuracy is less than the predefined value (operation 218), the system may: calculate, using information specifying the excitation and the accuracy as inputs to a second predetermined predictive model, a revised excitation (operation 222) that has at least a revised wavelength, a revised intensity or a revised flux; and repeat (operation 224) the applying, measuring, computing and determining operations with the revised excitation instead of the excitation. Note that the second predetermined predictive model may include a machine-learning model and/or a neural network.

In some embodiments, the system optionally performs one or more optional additional or alternative operations. For example, when the accuracy is less than the predefined value (operation 218), the system may: add the excitation and the measured response to a training dataset; and determine, using the training dataset, a revised instance of the predictive model.

Additionally, the system may classify or segment one or more anatomical structures in the sample using the model parameters and a third predictive model. For example, the third predetermined predictive model may include a machine-learning model and/or a neural network.

Moreover, the system may train the predictive model using a simulated dataset computed using the forward model, a range of model parameters and a range of excitations.

Figure 3:
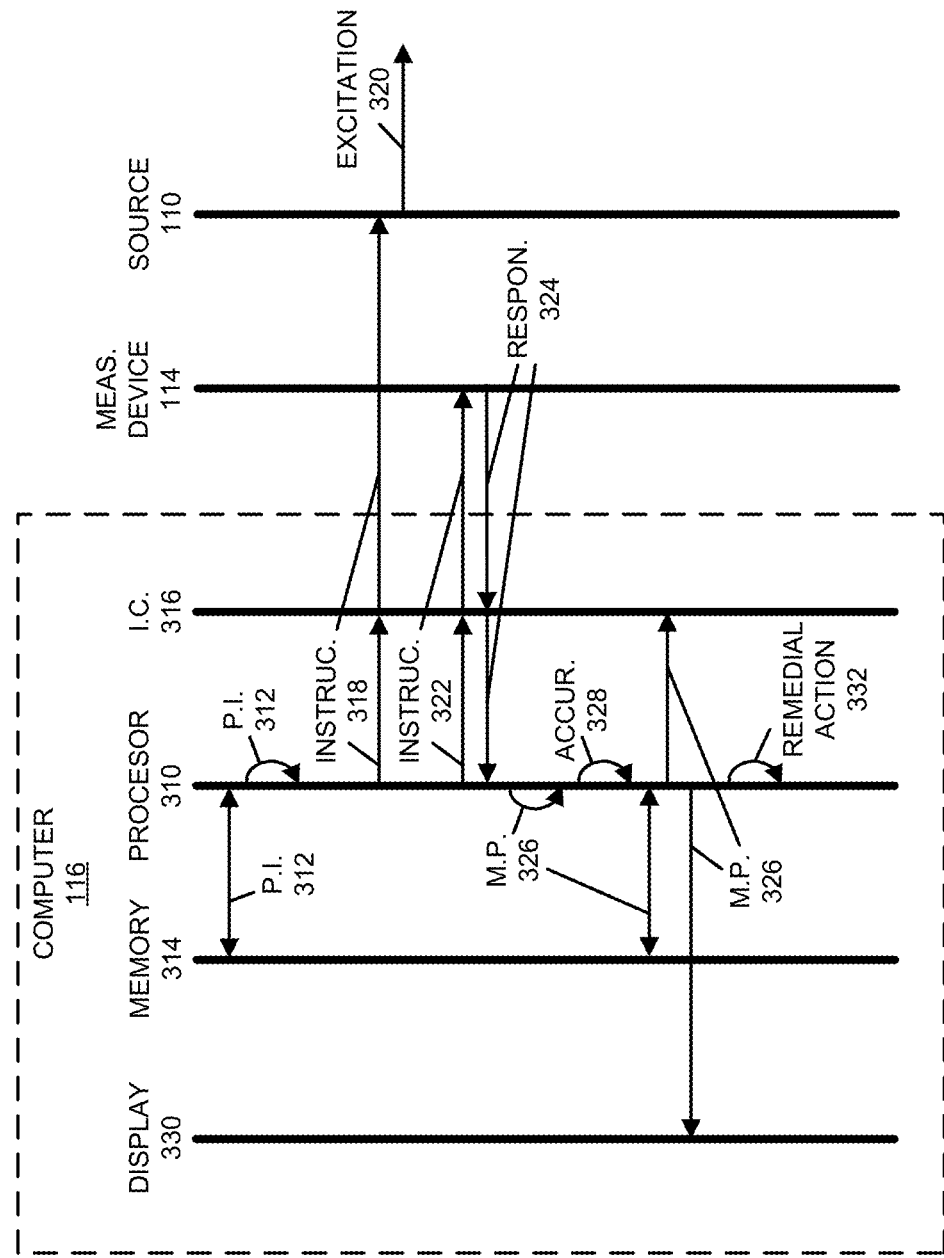
FIG. 3 is a drawing illustrating an example of communication among components in the system in FIG. 1 in accordance with an embodiment of the present disclosure.

FIG. 3 presents a drawing illustrating an example of communication among components in system 100 (FIG. 1). Notably, processor 310 in computer 116 may execute program instructions (P.I.) 312 stored in memory 314. When processor 310 executes program instructions 312, processor 310 may perform at least some of the operations in the computation technique.

During the computation technique, processor 310 may provide instruction 318 to interface circuit (I.C.) 316. In response, interface circuit 316 may provide instruction 318 to source 110, e.g., in one or more packets or frames. Moreover, after receiving instructions 318, source 110 may apply, to the sample, an excitation 320.

Then, processor 310 may provide instruction 322 to interface circuit 316. In response, interface circuit 316 may provide instruction 322 to measurement device 114, e.g., in one or more packets or frames. Furthermore, after receiving instructions 322, measurement device 114 may measure a response 324 associated with the sample to excitation 320. Next, measurement device 114 may provide measured response 324 to computer 116, e.g., in one or more packets or frames.

After receiving measured response 324, interface circuit 316 may provide measured response 324 to processor 310. Then, using measured response 324 and information specifying excitation 320 as inputs to a predetermined predictive model, processor 310 may compute model parameters (M.P.) 326 on a voxel-by-voxel basis in a forward model with multiple voxels that represent the sample.

Additionally, processor 310 may determine an accuracy 328 of the model parameters by comparing at least measured response 324 and a calculated predicted value of the response using the forward model, model parameters 326 and excitation 320. When accuracy 328 exceeds a predefined value, processor 310 may provide the model parameters 326 as, e.g., an output to a user, to another electronic device (via interface circuit 316), to a display 330 and/or memory 314.

Otherwise, when the accuracy is less than the predefined value, processor 310 may perform a remedial action 332. For example, processor 310 may: calculate, using information specifying excitation 320 and accuracy 328 as inputs to a second predetermined predictive model, a revised excitation; and repeat the applying, measuring, computing and determining operations with the revised excitation instead of excitation 320. Alternatively or additionally, processor 310 may: add excitation 320 and measured response 324 to a training dataset; and determine, using the training dataset, a revised instance of the predictive model.

We now describe embodiments of predictive models. For example, a predictive model may include a machine-learning model, such as a supervised-learning model or an unsupervised learning technique (such as clustering). In some embodiments, a machine-learning model may include: a support vector machine (SVM), a classification and regression tree, logistic regression, LASSO, LASSO logistic regression, linear regression, nonlinear regression, pattern recognition, a Bayesian technique, and/or another (linear or nonlinear) supervised-learning technique.

Figure 4:
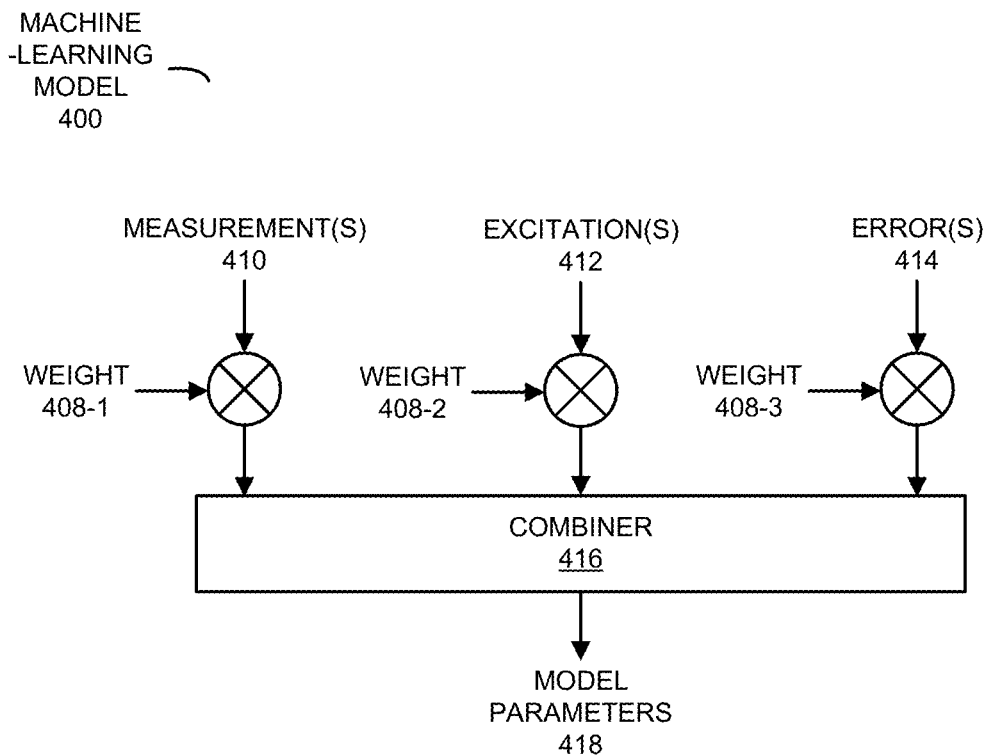
FIG. 4 is a drawing illustrating an example of a machine-learning model in accordance with an embodiment of the present disclosure.

FIG. 4 presents a drawing illustrating an example of a machine-learning model 400. In this machine-learning model, a weighted (using weights 408) linear or nonlinear combination 416 of measurements 410, one or more corresponding excitations 412 and one or more errors 414 between the one or more measurements 410 and one or more predicted responses determined using a forward model, a current instance of the model parameters of voxels in the forward model, and the one or more excitations 412 is used to compute a revised instance of model parameters 418. Thus, in some embodiments, predictive model 400 is used in conjunction with forward model to iteratively modify instances of the model parameters until an accuracy of the predicted response is less than a predefined value (i.e., a convergence criterion is achieved). However, in some embodiments, a machine-learning model may be used to determine the model parameters in one pass, i.e., in an open-loop manner.

Alternatively or additionally, a predictive model may include a neural network. Neural networks are generalized function approximators. For example, techniques such as deep learning typically use previous examples as inputs. In general, it is not possible for these machine-learning models to determine the actual function they are trying to approximate because there is no reference point for them to use to estimate the error in their predictions. In particular, it can be difficult for a neural network to make predictions based on an input that is very different from the examples it was trained on. In this regard, a neural network can be thought of as a lossy compute compression engine.

However, by training a neural network using a wide variety of excitations, measured responses and corresponding model parameters, the neural network can provide the model parameters (or initial estimates of the model parameters) for a forward model that simulates the physics of a response of a sample to an excitation. Because neural networks are effective approximations/compressions, they may execute faster on the same inputs with less computational power required. Moreover, because the functions are known in the forward model, the responses can be computed and the accuracy of the predictions can be assessed (as opposed to using an approximation). Therefore, the computation technique can be used to determine when its predictions are unreliable. In particular, as discussed previously for FIG. 4, a neural network may be used in conjunction with forward model to iteratively modify instances of the model parameters until an accuracy of the predicted response is less than a predefined value (i.e., a convergence criterion is achieved). In some embodiments, however, a neural network may be used to determine the model parameters in one pass, i.e., in an open-loop manner.

Figure 5:
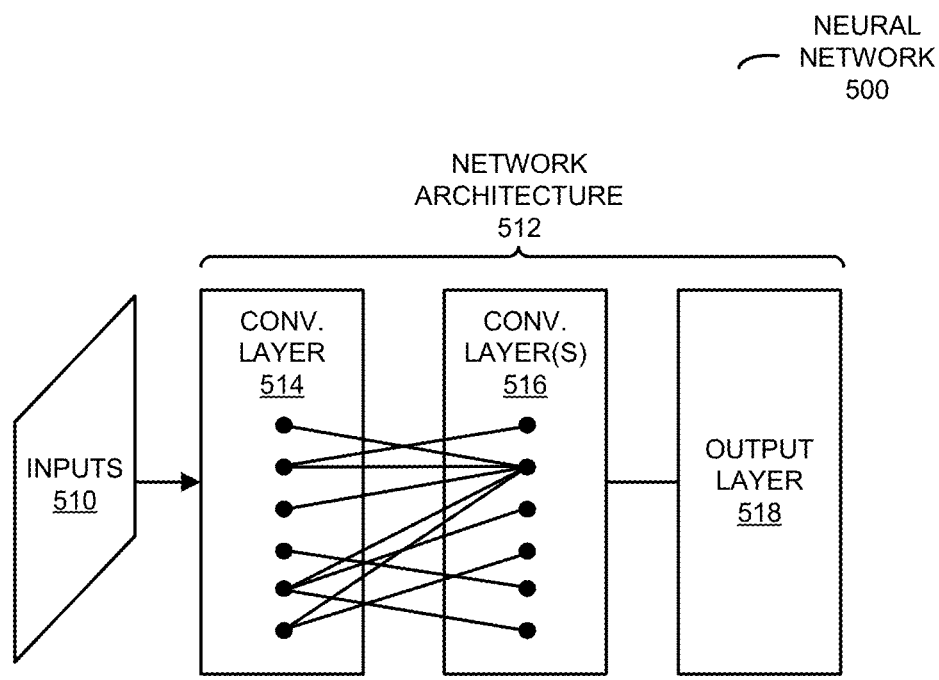
FIG. 5 is a drawing illustrating an example of a neural model in accordance with an embodiment of the present disclosure.

FIG. 5 presents a drawing illustrating an example of a neural network 500. This neural network may be implemented using a convolutional neural network or a recurrent neural network. For example, neural network 500 may include a network architecture 512 that includes: an initial convolutional layer 514 that provides filtering of inputs 510 (such as one or more measurements and a difference or an error between the one or more measurements and one or more predicted responses determined using a forward model, a current instance of model parameters and an excitation); an additional convolutional layer(s) 516 that apply weights; and an output layer 518 (such as a rectified linear layer) that performs selection (e.g., selecting a revised instance of the model parameters). Note that the details with the different layers in neural network 500, as well as their interconnections, may define network architecture 512 (such as a directed acyclic graph). These details may be specified by the instructions for neural network 500. In some embodiments, neural network 500 is reformulated as a series of matrix multiplication operations. Neural network 500 may be able to handle the real-world variance in 1 million inputs or more. Note that neural network 500 may be trained using a deep-learning technique or a GAN. In some embodiments of machine-learning model 400 (FIG. 4) and/or neural network 500, a current instance of the model parameters is used as an input.

In some embodiments, a large convolutional neural network may include 60 M parameters and 650,000 neurons. The convolutional neural network may include eight learned layers with weights, including five convolutional layers and three fully connected layers with a final 1000-way softmax or normalized exponential function that produces a distribution over the 1000 class labels for different possible model parameters. Some of the convolution layers may be followed by max-pooling layers. In order to make training faster, the convolutional neural network may use non-saturating neurons (such as a local response normalization) and an efficient dual parallelized GPU implementation of the convolution operation. In addition, in order to reduce overfitting in the fully-connected layers, a regularization technique (which is sometimes referred to as 'dropout') may be used. In dropout, the predictions of different models are efficiently combined to reduce test errors. In particular, the output of each hidden neuron is set to zero with a probability of 0.5. The neurons that are 'dropped out' in this way do not contribute to the forward pass and do not participate in backpropagation. Note that the convolutional neural network may maximize the multinomial logistic regression objective, which may be equivalent to maximizing the average across training cases of the log-probability of the correct label under the prediction distribution.

In some embodiments, the kernels of the second, fourth, and fifth convolutional layers are coupled to those kernel maps in the previous layer that reside on the same GPU. The kernels of the third convolutional layer may be coupled to all kernel maps in the second layer. Moreover, the neurons in the fully connected layers may be coupled to all neurons in the previous layer. Furthermore, response-normalization layers may follow the first and second convolutional layers, and max-pooling layers may follow both response-normalization layers as well as the fifth convolutional layer. A nonlinear model of neurons, such as Rectified Linear Units, may be applied to the output of every convolutional and fully-connected layer.

In some embodiments, the first convolutional layer filters a 224×224×3 input image with 96 kernels of size 11×11×3 with a stride of four pixels (this is the distance between the receptive field centers of neighboring neurons in a kernel map). Note that the second convolutional layer may take as input the (response-normalized and pooled) output of the first convolutional layer and may filter it with 256 kernels of size 5×5×48. Furthermore, the third, fourth, and fifth convolutional layers may be coupled to one another without any intervening pooling or normalization layers. The third convolutional layer may have 384 kernels of size 3×3×256 coupled to the (normalized, pooled) outputs of the second convolutional layer. Additionally, the fourth convolutional layer may have 384 kernels of size 3×3×192, and the fifth convolutional layer may have 256 kernels of size 3×3×192. The fully-connected layers may have 4096 neurons each. Note that the numerical values in the preceding and the remaining discussion below are for purposes of illustration only, and different values may be used in other embodiments.

In some embodiments, the convolutional neural network is implemented using at least two GPUs. One GPU may run some of the layer parts while the other runs the remaining layer parts, and the GPUs may communicate at certain layers. The input of the convolutional neural network may be 150,528-dimensional, and the number of neurons in the remaining layers in the convolutional neural network may be given by 253, 440-186, 624-64, 896-64, 896-43, and 264-4096-4096-1000.

We now describe embodiments of a forward model. This forward model may be a 3D model of voxels in a portion of a sample (such as an individual), and may include model parameters in the Bloch equations for each of the voxels. In particular, with a quasi-static magnetic field $B_0$ along the z axis, the Bloch equations are $$\frac{dM_x(t)}{dt} = \gamma \cdot (\vec{M}(t) \otimes \vec{B}(t))_x - \frac{M_x(t)}{T_2},$$

$$\frac{dM_y(t)}{dt} = \gamma \cdot (\vec{M}(t) \otimes \vec{B}(t))_y - \frac{M_y(t)}{T_2}, \text{ and}$$

$$\frac{dM_z(t)}{dt} = \gamma \cdot (\vec{M}(t) \otimes \vec{B}(t))_z - \frac{M_z(t) - M_0}{T_1},$$

where $\gamma$ is the gyromagnetic ratio, $\otimes$ denotes a vector cross product and $\vec{B}(t) = (B_x(t), B_y(t), B_0 + \Delta B_z(t))$ is the magnetic field experienced by a type of nuclei in the sample. The model parameters in the Bloch equations may include $T_1$, $T_2$, a density of a type of nuclei, diffusion, velocity/flow, temperature, magnetic susceptibility, etc. Note that there may be different model parameters for different types of nuclei for each of the voxels. Moreover, note that the Bloch equations are a semi-classical, macroscopic approximation to the dynamic response of the magnetic moments of the type of nuclei in the sample to a time-varying magnetic field. For example, there may be 67 M cells in a 1 mm$^3$ voxel.

In principle, the solution space for the model parameters in the Bloch equations for the sample may be underdetermined, i.e., there may be significantly more model parameters to be determined than there are observations with which to specify or constrain the model parameters. Therefore, when training a predictive model or determining the model parameters using the predictive model (such as using computations in a machine-learning model or in a layer in a neural network), the computation technique may leverage additional information to constrain or reduce the dimensionality of the problem. For example, an aspect of the anatomy of the sample may be determined using other imaging techniques, such as computed tomography, x-ray, ultrasound, etc. Moreover, regions that do not look like (i.e., that has very different measurements, e.g., different measured MR signals) than a targeted type of tissue (such as heart tissue) may be excluded from the forward model (such as by setting the model parameters to zero in these regions). In this way, e.g., regions that include air may be excluded. Other constraints in the forward model may include: thermodynamic constraints on heat flow (from hot to cold) for perfusion or MRT to quantify metabolism. In addition, the predictive model may be trained using measurements at different magnetic-field strengths $B_0$ (which may provide similar information to pseudorandom pulse sequences) using different pulse sequences and/or different MR techniques, which may reduce the ratio of model parameters to observations, thereby simplifying the training of the predictive model.

Alternatively or additionally, tissue that deviates significantly from a predicted or simulated response (such as predicted MR signals) based on previous MR measurements or scans (e.g., anomalies or changes) may become the focus of the forward model, such as by using a contour map (e.g., cubic spline) to bound the regions (or specify a boundary of the regions) where there are significant differences. In some embodiments, when training the predictive model or determining the model parameters using the predictive model (such as using computations in a machine-learning model or in a layer in a neural network), the difference or error between measurements and simulated or predicted responses may be represented using one or more level-set functions, and the boundaries of regions with errors exceeding a threshold value may be determined based on the intersection of a plane corresponding to the threshold value and the one or more level-set functions.

In some embodiments, a layer in a neural network may compute first and second derivatives along a surface(s) of model-parameter solutions in the sample. (In order to facilitate calculation of a derivative, the model parameters may be represented using one or more level-set functions.) A set of voxels along the line where the first derivative is zero may be identified. This set of voxels may be fit using a cubic spline with a minimum error between the voxel positions and the cubic spline. This fitting operation may be repeated at all the boundaries in the model-parameter-solution space. Moreover, the largest continuous surface within the boundary defined by the cubic splines may be determined and the model-parameter-solution calculation may be repeated to determine a new continuous surface that is within the previous continuous surface. This generalized framework may minimize the error across intra-voxel volumes, thereby improving the agreement between the measurements and the simulated or predicted responses based on the forward model.

For example, a neural network may solve the inverse problem using a Jacobian matrix of the model parameters for the voxels in the forward model and Newton's method to modify the model parameters for the voxels in successive layers based on how perturbations in the model parameters affect the difference or error between the measurements and the predicted responses.

In some embodiments, if a portion of the sample included one voxel, there may be 4-10 model parameters (which specify a forward model) that need to be determined for a particular type of tissue. If the voxel includes M types of tissue, there may be 4M-10M the model parameters that need to be determined for the particular type of tissue. As the number of voxels increases, this can appear to be a daunting problem.

However, because different types of nuclei have different Larmor frequencies, the spatial distribution of the types of nuclei and their local concentrations may be determined from the measurements. Then, a predefined anatomical template for the human body (or a portion of the human body), with associated initial model parameters for the forward model, may be scaled to match the spatial distribution of the types of nuclei and their local concentrations. For example, predetermined or predefined ranges for the model parameters in different types of tissue may be used to determine for the initial model parameters. In some embodiments, the initial model parameters are based on model parameters associated with previous measurements or MR scans.

Next, a look-up table with simulated or predicted responses (generated using one or more forward models) as a function of associated model parameters and excitations may be used modify the initial model parameters or to compute model parameters for voxels in the sample. For example, simulated or predicted responses that are similar to measurements may be identified, and the differences or errors between these simulated or predicted responses and the measurements may be used to guide interpolation between the model parameters in the look-up table.

In some embodiments, for a type of tissue (such as a particular organ), the model parameters determined using different layers in a neural network may be iteratively refined as the size of the voxels is progressively decreased (and, thus, the number of voxels is increased) in the different layers. This analysis may be driven by the error between the measurements and simulated or predicted responses using the forward model. Progressing through successive layers in a neural network, the focus may be on the residual regions with errors that are larger than a convergence or an accuracy criterion. For example, the model parameters for the forward model in a layer in a neural network may be based on measurements at one magnetic-field strength and then the error may be determined based on the predicted response of the forward model at another magnetic-field strength. Furthermore, note that initially the predictive model or the forward model may assume that there is no contribution or interaction between different voxels. However, as the error and the voxel size are reduced, such contributions and/or interactions may be included in subsequent layers in a neural network. In some embodiments, when there are multiple candidate model-parameter solutions (having similar errors) to the inverse problem for a layer in a neural network, at least some of these candidates may be kept for use in a subsequent layer (i.e., a unique model-parameter solution may not be identified at this point). Alternatively, if there is no unique parameter solution within a desired error range (such as less than 50, 25, 10, 5 or 1%), the best (least-error) model-parameter solution may be kept. In addition, when there is no model-parameter solution within the desired error range, the second predictive model may be used to modify the excitation and additional measurement(s) may be performed.

Thus, the inverse problem of determining the model parameters based on measurements may be 'solved' using a predictive model that provides model parameters that minimize the error or difference between the measurements and simulated or predicted responses that are generated based on the forward model, the model parameters and an excitation. In some embodiments, the inverse problem is solved using one or more analysis techniques, including: a least-squares technique, a convex quadratic minimization technique, a steepest descents technique, a quasi-Newton technique, a simplex technique, a Levenberg-Marquardt technique, simulated annealing, a genetic technique, a graph-based technique, another optimization technique and/or Kalman filtering (or linear quadratic estimation).

Note that the training of a predictive model may use dynamic programming. In particular, the training problem may be divided up and performed by multiple computers in parallel, e.g., in a cloud-based computing system. For example, a particular thread may attempt to solve the inverse problem for particular measurement conditions. Multiple potential model-parameter solutions generated by the computers (or processors) may be combined (e.g., using linear superposition) to determine an error metric that is minimized using the one or more analysis techniques.

Moreover, as described previously, the inverse problem may be solved iteratively by a predictive model (such as machine-learning model or a neural network) by first attempting to find suitable model parameters (e.g., model parameters that minimize the error between measurements and simulated or predicted responses) for the forward model using a coarse voxel size and then progressively finding suitable parameters with smaller voxel sizes in subsequent layers or stages of the calculation. Note that the final voxel size used in this iterative procedure (or a suitable range of voxel sizes, because the voxel size may not be fixed in some embodiments) may be determined based on the gyromagnetic ratio of a type of nuclei being scanned. Furthermore, the voxel size or locations may also be chosen so that a voxel is evenly portioned into a set of subvoxels, or so that there is certain amount of overlap with preview voxel sizes to effectively 'oversample' the overlapping region and potentially further localize where an MR signal originates. This last technique may be akin to shifting the entire gradient system in one or more dimensions by a distance dx that is less than a characteristic length of the voxels (such as a length, a width or a height of the voxels). In some embodiments, the voxel size in the predictive model or the forward model is smaller than that used in the measurements (i.e., the predictive model or the forward model may use a super-resolution technique). For example, there may be 512×512 voxels or 1024×1024 voxels at a magnetic-field strength of 3 T. Note that the voxel size may be less than $0.25^3$ mm$^3$.

We now describe embodiments of a technique for segmenting different types of tissue, which may be used by the third predictive model (such as a neural network). Define a dictionary $D_{mr}$ of measured time-sampled MR trajectories (or vectors) in a multi-dimensional parameter space for different types of tissue dj (for j=1 to n) such that a measured MR signal $y_{obv}$ for a voxel can be expressed as $$y_{obv} = \sum_{j=1}^{n} \alpha_j \cdot d_j + \varepsilon,$$

where $\alpha_j$ are normalized weights $$\left(\text{i.e., } \sum_{j=1}^{n} \alpha_j = 1\right)$$

and $\varepsilon$ is an error (i.e., $\varepsilon=(\gamma_j,\alpha_j)$, for j=1 to n. This may define an intra-voxel linear equation problem. A generalized inter-voxel problem may model a set of voxels (such as a cube with 27 voxels) as a graph G. Note that each voxel in the set may have 26 edges to eight adjacent voxels. A parameter solution to the inverse problem may be defined as one that minimizes the error.

Consider the case of two adjacent voxels u and v. The intra-voxel linear equations $U_y$ and $V_y$ need to be solved at both u and v. There are several possible outcomes. First, $U_y$ and $V_y$ may have unique model-parameter solutions (where a 'unique model-parameter solution' may be a best fit to an existing forward model, i.e., with an error or difference vector that is less than a convergence or an accuracy criterion) and the analysis may be finished. Alternatively, $U_y$ may have a unique model-parameter solution but not $V_y$. It may be possible that the model-parameter solution for $U_y$ imposes a constraint on $V_y$ such that $V_y$ has a single model-parameter solution, in which case the analysis may be finished. However, neither $U_y$ and $V_y$ may have unique model-parameter solutions, in which case combining the systems of equations (i.e., effectively increasing the voxel size) may yield a unique model-parameter solution. Moreover, neither $U_y$ and $V_y$ may have any model-parameter solutions, in which case the intra-voxel problem cannot be solved without further constraints.

In the last case, it may be possible to look at an adjacent voxel w, i.e., series voxels u, v and w, with the corresponding intra-voxel linear equations $U_y$, $V_y$ and $W_y$ need to be solved at u, v and w. Note that the intra-voxel linear equations $V_y$ and $W_y$ reduce to the previous case. When the intra-voxel linear equations do not reduce to the previous case, this paring operation can be applied recursively until it does and then the intra-voxel linear equations can be solved as described previously.

In general, this analysis technique may be isomorphic to the problem of fitting a 3D surface (or volume) to minimize the error. One challenge in this regard is that it assumes that all adjacent volumes have an equal effect on the model-parameter solution $\alpha_j$ that minimizes the error.

The minimization of the error may initially assume that there is no inter-voxel contribution (i.e., that the voxels are independent). Subsequently, inter-voxel contributions may be included. In particular, considering adjacent voxel volumes, there are two distinct classes. Volumes that share a surface and volumes that only share a 1D edge. The minimization function can be improved by weighting the error contribution at voxel u at the center of the relative coordinate system. If the effect on the error is proportional to $r^{-2}$ (where r is the distance between center points of voxels) and assuming 1 mm isotropic voxels in the weightings, the minimization or fitting problem with inter-voxel contributions can be expressed as $$\min\left(\text{error}\left(y(0,0,0),\alpha(0,0,0)+\frac{1}{(1)^2}\sum_{k=1}^{m}\text{error}(y_k,\alpha_k)+\frac{1}{(\sqrt{2})^2}\sum_{l=1}^{p}\text{error}(y_l,\alpha_l)\right.\right.$$

where the summation over k is for adjacent voxels sharing a common surface (i.e., (−1,0,0), (1,0,0), (0,−1,0), (0,1,0), (0,0,−1) and (0,0,1)) and the summation over l is for a remainder of adjacent voxels sharing a common edge. The assumption in the analysis is that the most difficult place to fit or determine model-parameter solutions is at discontinuities or interfaces between different tissues. Consequently, during the computation technique, analysis engine 122 (FIG. 1) may solve these locations first and then may solve the remaining locations.

Alternatively, because the magnetic contribution from neighboring voxels is proportional to $r^2$, given a sphere of radius R from the center of a primary or central voxel in the minimization problem, surrounding voxels may be weighted based on the how much the sphere expands into the volume of the adjacent voxels (and, thus, based on how strong their inter-voxel contribution is estimated to be). For example, there may be three different weights that need to be assigned, including: a weight for voxels that share a 2D surface, a weight for voxels that share a 1D line, and a weight for voxels that share a 0D point. Because there may not be a uniform tissue distribution within each voxel, the weights may be dynamically adjusted to model different kinds of distributions inside each voxel in order find the distributions that minimize the error. This may provide the ability to identify multiple MR signatures within a single voxel for different types of tissue. Note that, as computational power increases, the accuracy of the third predictive model may increase and the analysis technique used to solve the minimization problem (and, thus, the inverse problem) may be modified.

Thus, in embodiments where the forward model of a voxel depends on the forward models of surrounding or neighboring voxels, the forward model of a voxel may be computed using $2^{nd}$ or $N^{th}$-order effects. For example, if there are N−$1^{st}$-order forward models (where N is an integer), there may be as many as N!/(N−27)! $2^{nd}$-order forward models (if all the voxels interact with each other). In some embodiments, locality is used to simplify the inverse problem. In this way, a forward model may be generated by incorporating how the forward models in adjacent voxels effect the forward model in a primary (central) or $1^{st}$-order voxel.

In some embodiments, a dithering technique is used to overcome the arbitrary locations of the voxels relative to the distribution of types of tissue in the body. In particular, there may be two or more types of tissue in a voxel because of the arbitrary voxel placement or the current voxel size. This may significantly change the forward model parameters for this voxel. This may suggest that there is more than one forward model needed for the voxel. In order to confirm this, the voxels may be displaced by a distance dx (which is a fraction of the voxel length, width or height) and the forward model parameters may be determined again (e.g., using the predictive model). In the processes, the tissue distribution may be determined. Consequently, this approach may effectively increase the spatial resolution in the analysis without changing the voxel size.

Figure 6:
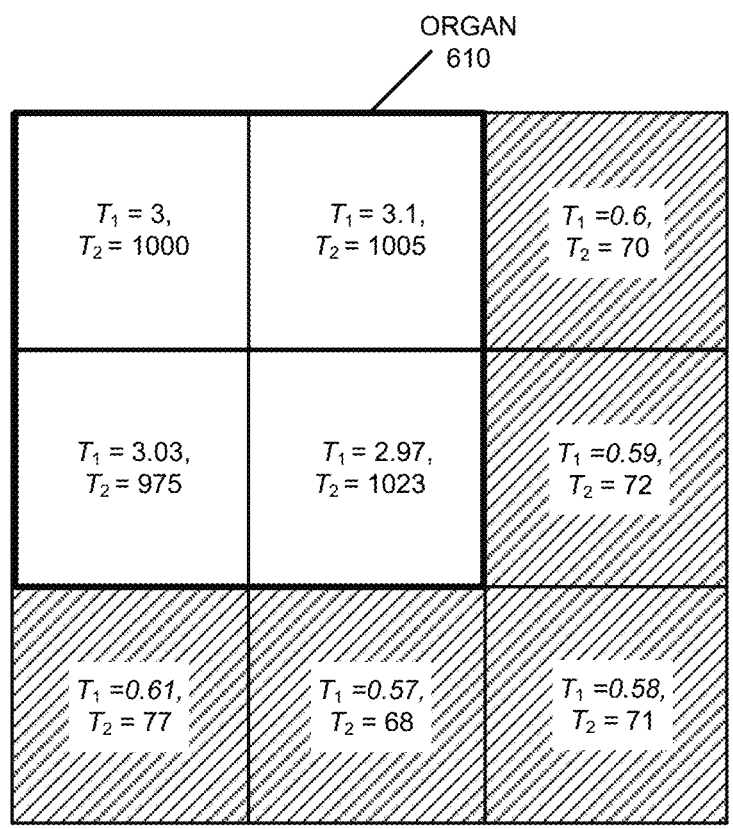
FIG. 6 is a drawing illustrating an example of classification or segmentation of one or more anatomical structures in the sample in accordance with an embodiment of the present disclosure.

FIG. 6 presents a drawing illustrating an example of classification or segmentation of one or more anatomical structures 600. Notably, FIG. 6 illustrates identifying or segmenting an organ 610 based at least in part on discontinuous changes in $T_1$ and $T_2$ at voxel boundaries.

While the preceding discussion illustrated the computation technique using MR techniques, this approach may be generalized to a measurement system that is able to physically model and measure a sample in real-time using a wide variety of characterization techniques. In general, the computation technique can use a combination of mechanical and/or electromagnetic waves to 'perturb' or 'excite' the volume being scanned in order to evaluate the correctness of a prediction in terms of how the volume responds to the perturbation. This also includes the ability for the system to simulate itself and any part of the environment in which the system is located that could affect the correctness or accuracy of the forward model the system is trying to generate to describe the volume being scanned or measured.

Note that the different characterization techniques may provide tensor-field mapping and the ability to detect anomalies in tensor fields. These maps can be images or quantitative tensor field maps, and each of the characterization techniques may provide a visualization of a different type of tensor field map captured with different type of measurements. By looking at or considering two or more of these maps, of the system may have access to orthogonal information.

Thus, the system may provide a way to capture, in real-time or near real-time, higher-order or hyper-dimensional pseudo or hybrid tensors or matrices at each voxel in 3D space. Using electromagnetic and/or mechanical perturbations or excitations, the system may use different characterization techniques to measure disturbances and responses, and then to simulate the responses.

The result of this characterization may be a (4+N)D (three spatial dimensions, one time dimension, and up to N measurement dimensions at each point in space) quantitative model of the volume being scanned. Note that the (4+N)D quantitative model may be projected onto an arbitrary subset of the full (4+N)D space, including 2D or 3D images.

In some embodiments, the use of multidimensional data and models provides enhanced diagnostic accuracy (i.e., a lower false-positive rate) relative to conventional MRI approaches, even if a larger voxel size is used. Thus, the computation technique may allow improved diagnostic accuracy with a larger voxel size (or a weaker external magnetic field) than would be needed in conventional MRI. However, as noted previously, the computation technique may be used with a wide variety of measurement techniques separately from or in addition to MRI.

In some existing MR scanners, multiple receive channels (with receivers and associated antennas) are used to accelerate or reduce the time needed to perform an MR scan. These approaches are sometimes referred to as 'MRI parallel imaging.'

Notably, the gradient coils in an MR scanner phase encode (temporally) MR signals, which allows the output MR signals to be distinguished from each other. Moreover, when there are multiple receive channels, there is redundancy in the collected phase-encoded MR signals. In principle, by exploiting the different phase profiles, the redundancy allows some of the phase-encoded MR signals (such as some of the MR scan lines) to be skipped and subsequently reconstructed from the other phase-encoded MR signals, thereby accelerating the MR scan time.

For example, for a 2D space, during an MR scan an RF pulse may be applied, and then the gradient coils in x and y may be opened and an MR scan line in k-space may be read out. These operations (applying an RF pulse and reading out an MR scan line) may then be repeated multiple times for additional MR scan lines (which have different phase encodings) until, e.g., 256 MR scan lines are read out. By using, e.g., 32 receive channels and skipping the measurement of some of these MR scan lines, the MR scan time can be reduced by, e.g., a factor of 2 or 3×.

Note, however, that the reduction in the MR scan time is not a linear function of the number of receive channels. This is because in many MRI parallel imaging techniques additional information is needed to reconstruct the skipped MR scan lines. Consequently, the reduction in the number of MR scan lines is either less than the number of receive channels or a separate pre-scan is used to acquire the additional information.

Notably, there are two principal classes of existing MRI parallel imaging techniques. A first class of approaches (which is referred to as 'SENSE', 'ASSET', 'RAPID' or 'SPEEDER') is image domain based after reconstruction of MR signals from individual RF pickup coils or antennas in receive channels (which are sometimes referred to as 'coils'). In this approach, the number of dropped or skipped MR scan lines may equal the number of receive channels. However, a separate pre-scan is used to determine the coil sensitivities (or coil sensitivity maps) of the receive channels. This is because the measured MR signal using a given receive channel during an MR scan corresponds to a volume integral of the product of a coil sensitivity for the given receiver channel and the time-dependent magnetization of the sample. Moreover, because the polarized magnetic field received by a coil or antenna in the given receive channel depends on its position and orientation, in general each of the coils or antennas in the receive channels has a different coil sensitivity. By performing a pre-scan, the coils sensitivities can be predetermined. Then, in the image domain, sample properties (such as the spatially varying proton density) can be illustrated or presented.

Thus, in existing MRI scanners, the first class of approaches may involve the operations of: generating coil sensitivity maps, acquire partial k-space MR data, reconstruct partial field-of-view images from each coil, and unfold/combine partial field-of-view images using matrix inversion. Note, therefore, that the first class of approaches is recast as a linear problem, and which may, in part, be solved using a Fourier transform and an inverse Fourier transform.

A second class of approaches (which is referred to as 'GRAPPA') is k-space based. This class of approaches may not use a pre-scan to determine the coil sensitivities. Instead, extra or additional MR scan lines may be acquired near k equal to zero in k-space. By leveraging the smoothness of these so-called 'auto-calibration lines' near k equal to zero, the missing (skipped) MR scan lines may be calculated (e.g., by interpolation using the auto-calibration lines).

Thus, in existing MR scanners, the second class of approaches may involve reconstructing the Fourier plane of an image from the frequency signals of each coil (i.e., reconstruction in the frequency domain). Note, once again, that the second class of approaches is recast as a linear problem, and which may, in part, be solved using a Fourier transform and an inverse Fourier transform.

In addition, there are some other (less common) approaches for MRI parallel imaging. Notably, the coil sensitivities and the sample properties (such as the spatially varying proton density) can be determined concurrently (instead of, e.g., using a pre-scan) in a joint reconstruction. For example, in principle, the coil sensitivities and the spatially varying proton density can be calculated from MR signals by solving a nonlinear inversion or inverse problem. However, this nonlinear optimization problem is typically ill defined (e.g., there is no unique solution because it is underdetermined, with more unknowns than can be specified by the measured MR signals).

One approach to solving the nonlinear optimization problem is to use an assumed regularizer to constrain the optimization. For example, the coil sensitivities may be assumed to be smooth. This constraint may allow solutions to be obtained, but in general the analysis time is often very long.

Another approach to solving the nonlinear optimization problem is to assume that the coil sensitivities can be represented as a linear superposition of polynomial functions. However, this assumed expansion is often ill-conditioned. Notably, it can be difficult to solve the nonlinear optimization problem with polynomial functions that are higher order than quadratic.

In embodiments of the disclosed computation technique, the nonlinear optimization problem may be solved without assuming that the coil sensitivities are smooth, are a linear superposition of polynomial functions, or have any pre-defined closed-form functional representations. Instead, the coil sensitivities may be solutions to Maxwell's equations (i.e., may satisfy Maxwell's equations and, thus, may not be approximations) in the field-of-view of an MR apparatus at a given external magnetic field strength. In addition to being physically accurate, the resulting coil sensitivities may allow the nonlinear optimization problem to be solved much more rapidly than existing nonlinear optimization approaches. Separately or in conjunction with skipped MR scan lines, this capability may significantly reduce an MR scan time.

Furthermore, because the disclosed computation technique (which is sometimes referred to as 'Maxwell parallel imaging') does not involve the use of a pre-scan to determine the coil sensitivities or the measurement of auto-calibration lines, Maxwell parallel imaging may be significantly faster than the first class of approaches and/or the second class of approaches described previously for MRI parallel imaging. For example, the MR scan time with Maxwell parallel imaging may be, e.g., at least 2-4× faster than these existing classes of approaches. Indeed, Maxwell parallel imaging may achieve a theoretical limit for the possible acceleration in the MR scan time for a given set of coils, a field-of-view, an external magnetic field strength (or resolution), and for a 2D or a 3D measurement.

Note that Maxwell parallel imaging may be used to accelerate the MR scan time with qualitative or quantitative MR measurements. Thus, Maxwell parallel imaging may be used with MRI, MR fingerprinting, tensor field mapping and/or another MR measurement technique.

In general, the solutions to Maxwell's equations for the coil sensitivities are circularly polarized magnetic fields. These coil magnetic fields may be generated in offline (i.e., not during an MR scan) using numerical simulations in the field-of-view of an MR apparatus. For example, the coil magnetic fields may be calculated by a distribution of currents (such as dipoles) on a surface surrounding the field-of-view in an MR apparatus. In some embodiments, there may be tens of thousands or more random currents on the surface.

However, because of the low frequency (the precession frequency for a proton in an external magnetic field of 1.5 T is 63.87 MHz) and the near-field condition, the currents on the surface may be similar to each other. Consequently, there may be a set of coil magnetic field basis vectors that encompasses or includes the majority of the energy or power in the different coil magnetic fields. For example, a singular value decomposition or an eigenvalue-decomposition technique may be used on the different numerically simulated coil magnetic fields to determine the set of coil magnetic field basis vectors. Then, a given coil magnetic field (and, thus, a given coil sensitivity) may be a linear superposition of the set of coil magnetic field basis vectors. In some embodiments, the set of coil magnetic field basis vectors may include, e.g., 30 coil magnetic field basis vectors. Note, once again, that the coil magnetic field basis vectors may each be a solution to Maxwell's equations. Alternatively, in some embodiments, the coil magnetic field basis vectors may each be an approximation to a solution to Maxwell's equations (such as within 85, 95 or 99% of a solution to Maxwell's equations).

By using the set of coil magnetic field basis vectors, the nonlinear optimization problem may be physically 'regularized' and may be solved in much less time. For example, if no regularization assumption is made, the nonlinear optimization problem for a 2D MR scan with 12 coils and having a 256-bit Fourier transform resolution may involve solving $256^2+12\cdot256^2$ unknown parameters. The first term of unknowns corresponding to, e.g., the unknown proton density and the second term of unknowns corresponding to the unknown coil sensitivities. As noted previously, this problem is ill-posed, so there is no unique solution and various approximations or assumptions have been used in some of the existing approaches.

In contrast, in Maxwell parallel imaging, instead of solving for the unknown coil sensitivities, the nonlinear optimization problem is determining the coefficients for the different coils in weighted linear superpositions of the set of coil magnetic field basis vectors. Thus, the nonlinear optimization problem for a 2D MR scan with 12 coils, 30 coil magnetic field basis vectors and having a 256-bit Fourier transform resolution may involve solving $256^2+12\cdot30$ unknown parameters. Therefore, Maxwell parallel imaging may much more rapidly (than existing approaches) solve, e.g., for the unknown proton density and the unknown coil sensitivities, because instead of solving for the unknown coil sensitivities, Maxwell parallel imaging concurrently calculates the coefficients for the set of coil magnetic field basis vectors and, e.g., the proton densities.

Note that in Maxwell parallel imaging a given coil sensitivity may be represented by or equal to a weighted superposition of the set of coil magnetic field basis vectors (i.e., a linear superposition of the products of the coefficients and the corresponding coil magnetic field basis vectors). Moreover, note that Maxwell parallel imaging may more accurately determine the coil sensitivities because, ultimately, it may involve solving Maxwell's equations for physical solutions (the set of coil magnetic field basis vectors) without assumptions. Furthermore, even though the weighted superposition of the set of coil magnetic field basis vectors may be an approximation to a given coil sensitivity, it may be a more-accurate and a physical representation.

In Maxwell parallel imaging, the nonlinear optimization problem may involve iteratively solving (e.g., minimizing) a data fidelity term (the squared absolute value of the difference of the MR signals minus estimated MR signals) subject to constraints. Note that the data fidelity term may incorporate or include a contribution from the coil sensitivities (such as the weighted superpositions of the set of coil magnetic field basis vectors). Moreover, note that the constraints may include: a structure of the spatial distribution of proton or nuclei density (and, more generally, an MR parameter, such as a nuclei density, a relaxation time, etc.), a total variation in the proton density (or an MR parameter), and/or another appropriate regularizer on the proton density (or an MR parameter). In general, the regularization term(s) on the proton density (or an MR parameter) may correspond to those used in image processing. Consequently, the regularization term(s) on the proton density (or an MR parameter) may avoid an L2 norm or a smoothing criterion.

In some embodiments, the nonlinear optimization problem may be solved using a predefined or pretrained neural network or a predefined or pretrained machine-learning model. In these embodiments, the coil sensitivities may, once again, be represented by the weighted superpositions of the set of coil magnetic field basis vectors.

Figure 7:
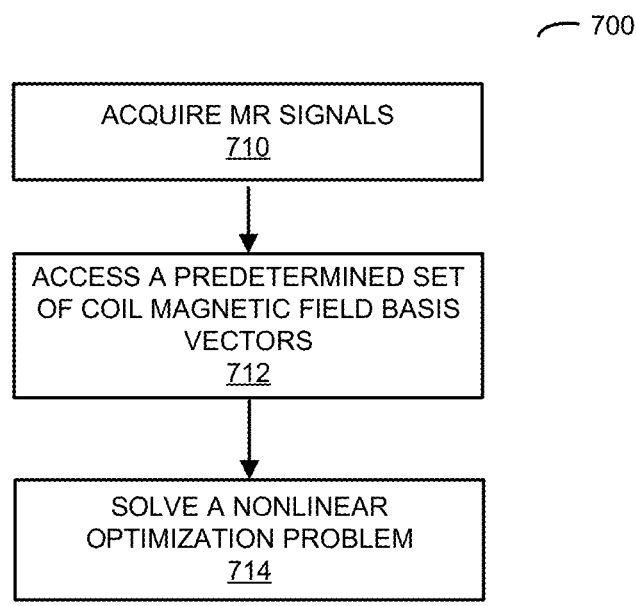
FIG. 7 is a flow diagram illustrating an example of a method for determining coefficients in a representation of coil sensitivities and MR information associated with a sample in accordance with an embodiment of the present disclosure.

FIG. 7 presents a flow diagram illustrating an example of a method 700 for determining coefficients in a representation of coil sensitivities and MR information associated with a sample. This method may be performed by a system (such as system 100 in FIG. 1), or one or more components in a system (such as source 110, measurement device 114 and/or computer 116 or, more generally, a computer system that includes one or more computers).

During operation, a computer system may acquire MR signals (operation 710) from or associated with a sample. This may involve having an MR apparatus applying an external magnetic field, a gradient magnetic field, and/or one or more RF pulse sequences, and measuring MR signals using receivers or receive channels. Alternatively or additionally, the computer system may access MR signals stored in memory, which were previously acquired by an MR apparatus or measurement device. Note that the MR apparatus may be located remotely from the computer system or may be proximate to the computer system (such as at a common facility).

Then, the computer system may access (e.g., in memory) a predetermined set of coil magnetic field basis vectors (operation 712), where weighted superpositions of the predetermined set of coil magnetic field basis vectors may represent coil sensitivities of coils in the MR apparatus. For example, a given coil sensitivity may be represented by a linear superposition of products of coefficients and predetermined coil magnetic field basis vectors in the predetermined set of coil magnetic field basis vectors. Note that each of the predetermined coil magnetic field basis vectors may be solutions to Maxwell's equations.

Next, the computer system may solve a nonlinear optimization problem (operation 714) for MR information associated with the sample and the coefficients using the MR signals and the predetermined set of coil magnetic field basis vectors. For example, the computer system may reduce or minimize a term corresponding to a squared absolute value of a difference between the MR signals and estimated MR signals. The term may include or may incorporate a contribution from the coil sensitivities of the coils in the MR apparatus. For example, a given coil sensitivity may be represented by a weighted superpositions of the predetermined set of coil magnetic field basis vectors, where the weights may include coefficients for each of the predetermined coil magnetic field basis vectors. Moreover, the estimated MR signals may correspond to MR information (such as a spatial distribution of one or more MR parameters in voxels, e.g., a proton or nuclei density, a relaxation time, etc.) specified by the MR signals. Furthermore, the nonlinear optimization problem may include one or more constraints on the reduction or minimization of the term, such as one or more constraints corresponding to the spatial distribution of the one or more MR parameters (e.g., a regularizer corresponding to the one or more MR parameters).

In some embodiments, the nonlinear optimization problem is solved iteratively (e.g., until a convergence criterion is achieved). However, in other embodiments, the nonlinear optimization problem is solved using a pretrained neural network or a pretrained machine-learning model that maps the MR signals and the set of coil magnetic field basis vectors to the spatial distribution of the one or more MR parameters (such as in voxels) and the coefficients. Thus, in some embodiments, the nonlinear optimization problem may be solved without iteration.

Moreover, in some embodiments, the spatial distribution of the one or more MR parameters specify a spatial distribution of nuclei density in the sample (e.g., in an image). Thus, in some embodiments, the MR signals may be determined in qualitative measurements, such as MRI or another MR measurement technique. In these embodiments, therefore, the MR apparatus may be an MR scanner.

Alternatively, in some embodiments, the spatial distribution of the one or more MR parameters may correspond to the model parameters discussed previously. Therefore, in some embodiments, the MR signals may be determined in quantitative measurements, such as TFM, MR fingerprinting or another quantitative MR measurement technique.

Figure 8:
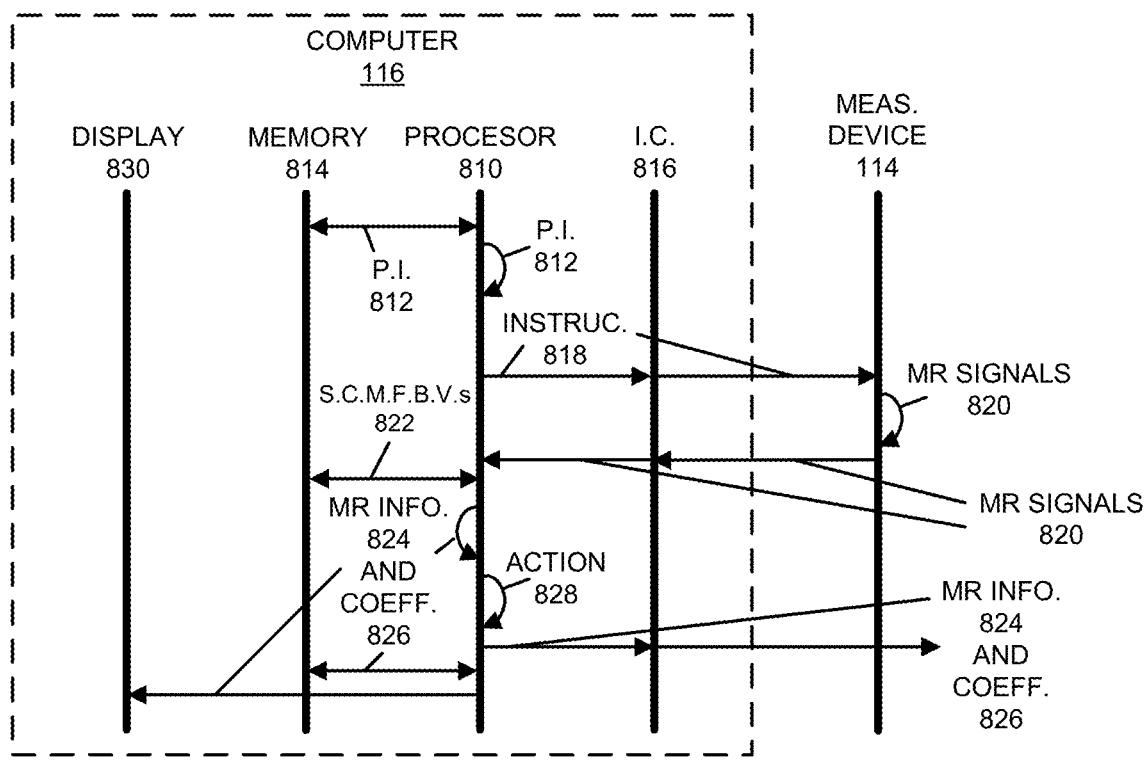
FIG. 8 is a drawing illustrating an example of communication among components in the system in FIG. 1 in accordance with an embodiment of the present disclosure.

FIG. 8 presents a drawing illustrating an example of communication among components in system 100 (FIG. 1) and measurement device 114. Notably, processor 810 in computer 116 may execute program instructions (P.I.) 812 stored in memory 814. When processor 810 executes program instructions 812, processor 810 may perform at least some of the operations in the computation technique.

During the computation technique, processor 810 may provide instruction 818 to interface circuit (I.C.) 816. In response, interface circuit 816 may provide instruction 818 to measurement device 114 (such as an MR apparatus) to acquire MR signals 820 associated with a sample, which are then provided to computer 116. Note that in some embodiments measurement device 114 may include a source, such as a source that provides an external magnetic field, a gradient magnetic field and/or an RF pulse sequence to the sample.

After receiving MR signals 820, interface circuit 816 may provide MR signals 820 to processor 810. Then, processor 810 may access in memory 814 a predetermined set of coil magnetic field basis vectors (S.C.M.F.B.V.s) 822, where weighted superpositions of the predetermined set of coil magnetic field basis vectors 822 may represent coil sensitivities of coils in measurement device 114, and a given predetermined coil magnetic field basis vector may be a solution to Maxwell's equations.

Next, processor 810 may solve a nonlinear optimization problem for MR information 824 on a voxel-by-voxel basis in the sample and coefficients 826 in the weighted superpositions using MR signals 820 and the set of predetermined set of coil magnetic field basis vectors 822. Moreover, processor 810 may perform an additional action 828. For example, processor 810 may: provide MR information 824 and/or coefficients 826 to a user or another electronic device via interface circuit 816, store MR information 824 and/or coefficients 826 in memory 814, and/or may present MR information 824 and/or coefficients 826 on a display 830.

In some embodiments, the computation technique addresses the problem of MRI reconstruction using multiple MR coils and under-sampled k-space measurements. By solving this problem, the computation technique may significantly reduce the MR acquisition or scan time, but without compromising the quality of the restored or reconstructed image. This problem is known as 'parallel imaging' or MRI parallel imaging.

Because of the limited or reduced number of k-space measurements and the presence of noise, the problem that the computation technique solves is ill-posed. This means that a unique solution does not exist and, in order to obtain a physically meaningful solution, additional prior knowledge about the properties of the underlying weighted proton-density (WPD) (which is sometimes referred to as the proton density or the nuclei density in the previous discussion) may need to be exploited. Furthermore, another challenge with parallel imaging is that, in addition to the WPD, which is the quantity for which an accurate estimate is desired, the MR coil sensitivities are also unknown.

In order to address this problem, the computation technique or the Maxwell parallel imaging technique may solve a bilinear problem with respect to the WPD and the coil sensitivities using an iterative Gauss-Newton regularized technique. For example, the computation technique may include an explicit regularizer on the WPD and an implicit regularizer on the coil sensitivities.

In some embodiments, the regularizer on the WPD can be of quadratic form and involve as a regularization operator: an identity operator, a gradient, a Hessian, a Laplacian or a non-smooth convex regularizer (such as the total variation or the structure total variation. In the case of a quadratic regularizer, because the data fidelity term is also quadratic, an iterative solution may be obtained by solving the augmented Gauss-Newton normal equations. For example, the augmented Gauss-Newton normal equations may be solved by using a conjugate gradient technique. Alternatively, when the regularizer on the WPD is a non-smooth convex functional, then the solution in each Gauss-Newton iteration may be obtained by employing an accelerated proximal gradient technique (such as FISTA).

Moreover, the implicit regularization of the coil sensitivities may be different from existing approaches. Notably, the implicit regularization of the coil sensitivities may enforce that the resulting coil sensitivities (which are essentially the circularly polarized magnetic fields that the coils receive) be smooth. In the implicit regularization of the coil sensitivities, a stronger, physics-based constraint may be imposed. More specifically, a complete (up to a numerical accuracy of, e.g., 85, 95 or 99%) basis of the circularly polarized magnetic fields may be generated. This basis may be supported in the filed-of-view of an MR scanner (or, more generally, an MR apparatus) for a given set of MR coils. For example, the basis may be determined using a randomized singular value decomposition of a matrix that maps the circularly polarized magnetic fields within the field-of-view from a set of tens of thousands or more dipole sources on a surface that encloses the field-of-view and is located close to the given MR coils. The calculation of the magnetic fields by these current sources may involve the use of a full-wave electromagnetic solver that uses of a state-of-the-art volume integral equation technique.

Consequently, in the resulting nonlinear optimization problem, the coefficients of this basis may be determined, instead of the actual coil sensitivities or magnetic fields. This approach may guarantee that the coil sensitivities are not only smooth, but that they satisfy, by construction, Maxwell equations, which is a much stronger constraint (and much closer to reality). Moreover, because of the smoothness of the coil sensitivities, only a small number of the members of this basis may be needed for high-fidelity coil sensitivity estimation. This capability may translate into orders of magnitude fewer parameters in the associated nonlinear optimization problem. Furthermore, the Maxwell parallel imaging technique may be applicable to an arbitrary (i.e., any) magnetic field strength of an MR scanner or an MR apparatus (e.g., from a few milliTesla to 11 Tesla or stronger external magnetic field strengths) without modification.

Thus, the Maxwell parallel imaging technique may provide an estimate of the WPD and an accurate estimate of the coil sensitivities. In order to further enhance the quality of the WPD image or results, in some embodiments, the WPD image may be denoised by solving a constrained optimization problem. Notably, a solution that minimizes the total variation or the structure total variation under the constraint that the norm of the difference of the input and the solution is less than or equal to a quantity that is proportional to the standard deviation of the noise. Note that the standard deviation may be computed directly from the WPD that was estimated previously in the Maxwell parallel imaging technique.

Alternatively, the estimated coil sensitivities, which were determined previously in the Maxwell parallel imaging technique, may be used to cast the original nonlinear problem into a linear one. This linear problem may still be ill-posed, because of the under-sampling of the k-space. Then, a final estimate of the WPD image may be obtained as the solution of a constrained convex optimization problem. Notably, the improved estimate of the WPD image may correspond to a minimizer of the total variation or the structure total variation subject to multiple constraints, whose number may equal to the number of MR coil measurements. Each of the constraints may enforce that the norm of the difference of the coil measurement and the corresponding observation or estimation model, which involves the solution, is less than or equal to a quantity proportional to the standard deviation of the noise effecting the specific coil measurements. These operations may provide a parameter-free denoising technique.

Figure 9:
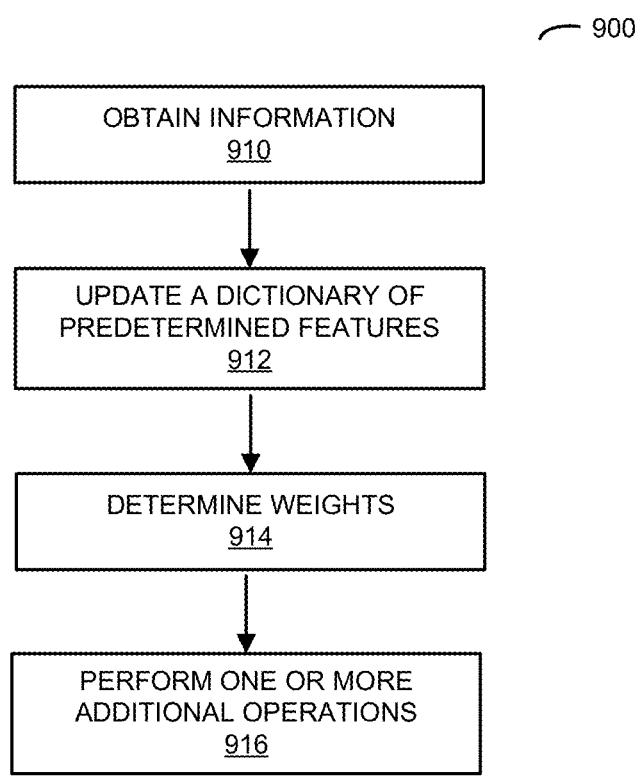
FIG. 9 is a flow diagram illustrating an example of a method for performing a sparsity technique in accordance with an embodiment of the present disclosure.

We now describe embodiments of sparsity techniques and sampling patterns. FIG. 9 presents a flow diagram illustrating an example of a method 900 for performing a sparsity technique. This method may be performed by a system (such as system 100 in FIG. 1), or one or more components in a system (such as computer 116 or, more generally, a computer system that includes one or more computers).

During operation, a computer system may access or obtain information (operation 910) associated with non-invasive measurements performed on an individual, historical non-invasive measurements, and a dictionary of predetermined features or basis functions associated with the historical non-invasive measurements.

Note that the non-invasive measurements and the historical non-invasive measurements may include or correspond to MR measurements. For example, the MR measurements may include MRI scans. Moreover, the non-invasive measurements and the historical non-invasive measurements may include MR parameters associated with voxels in the individual. For example, the parameters may include: a density of a type of nuclei, a longitudinal relaxation time along a direction parallel to an external magnetic field and/or a transverse relaxation time along a direction perpendicular to the external magnetic field.

Additionally, the historical non-invasive measurements may be associated with the individual or a group of individuals. In some embodiments, the group of individuals may exclude the individual. For example, the individual and the group of individuals may share one or more characteristics or attributes, such as: age, demographics, residential location, profession, education (e.g., a highest level of education), family history, ancestry, medical history (e.g., a type of disease or a risk for developing a type of disease), etc.

Then, the computer system may update the dictionary of predetermined features (operation 912) based at least in part on the non-invasive measurements and the historical non-invasive measurements, where the updating includes performing a minimization technique with a cost function having an L2-norm term and an L0-norm term.

Next, the computer system may determine weights (operation 914) associated with features in the updated dictionary of predetermined features based at least in part on the non-invasive measurements. Note that determining the weights may include a gradient-descent technique. Moreover, the dictionary of predetermined features and the updated dictionary of predetermined features may correspond to a portion of an anatomy of the individual.

In some embodiments, the computer system may perform one or more optional additional operations (operation 916). For example, the non-invasive measurement may include at least a component of a magnetization associated with the individual, and the computer system may: calculate at least a predicted component of the magnetization for the voxels associated with the individual based at least in part on the measured component of the magnetization, a forward model, the external magnetic field and the RF pulse sequence; and solve an inverse problem by iteratively modifying the parameters associated with the voxels in the forward model until a difference between the predicted component of the magnetization and the measured component of the magnetization is less than a predefined value.

In some embodiments of method 200 (FIG. 2), 700 (FIG. 7) and/or 900, there may be additional or fewer operations. Furthermore, the order of the operations may be changed, and/or two or more operations may be combined into a single operation.

Figure 10:
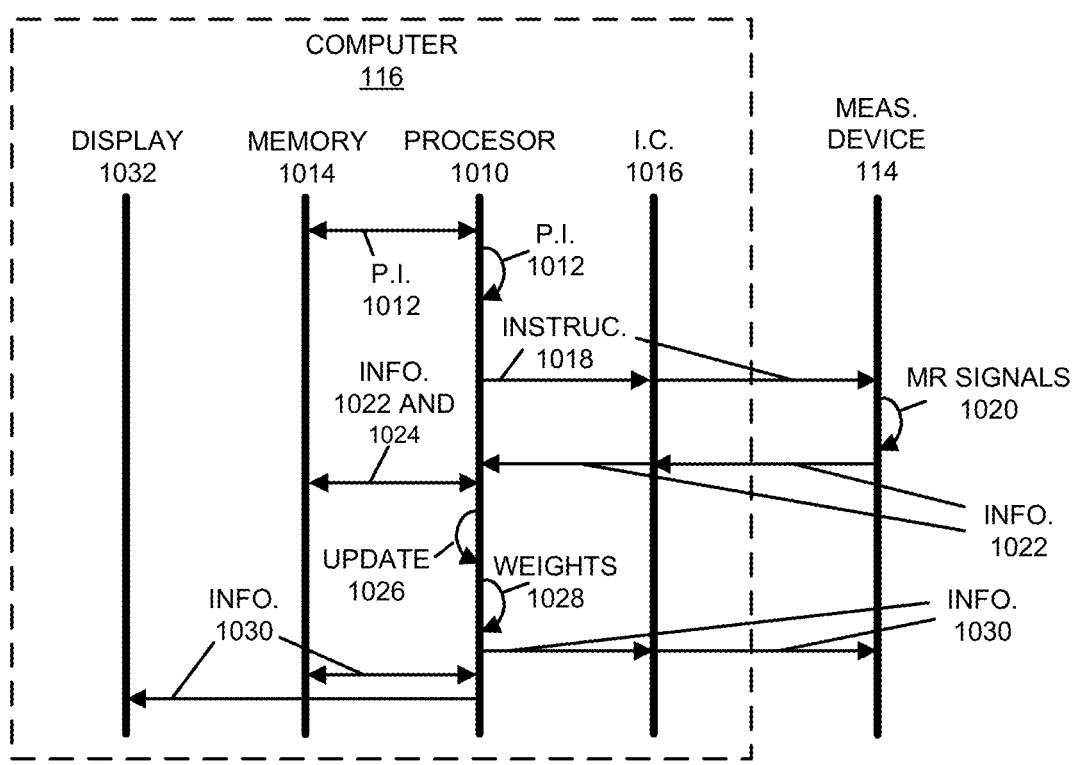
FIG. 10 is a drawing illustrating an example of communication among components in the system in FIG. 1 in accordance with an embodiment of the present disclosure.

FIG. 10 presents a drawing illustrating an example of communication among components in system 100 (FIG. 1) and measurement device 114. Notably, processor 1010 in computer 116 may execute program instructions (P.I.) 1012 stored in memory 1014 in computer 116. When processor 1010 executes program instructions 1012, processor 1010 may perform at least some of the operations in the analysis techniques.

During the analysis techniques, processor 1010 may provide instruction 1018 to interface circuit (I.C.) 1016 in computer 116. In response, interface circuit 1016 may provide instruction 1018 to measurement device 114 (such as an MR apparatus) to acquire MR signals 1020 associated with a sample (such as an MRI scan). Then, measurement device 114 may provide information 1022 that specifies or that correspond to (are a function of) MR signals 1020 to computer 116. Note that in some embodiments measurement device 114 may include a source, such as a source that provides an external magnetic field, a gradient magnetic field and/or an RF pulse sequence to the sample. After receiving MR signals 1020, interface circuit 1016 may provide information 1022 to processor 1010.

Alternatively or additionally, processor 1010 may access in memory 1014 information 1022. Moreover, processor 1010 may access in memory 1014 information 1024 that specifies historical MR signals (such as historical MRI scans), and a dictionary of predetermined features or basis functions associated with the historical MR signals.

Then, processor 1010 may update 1026 the dictionary of predetermined features (operation 912) based at least in part on MR signals 1020 and the historical non-invasive measurements, where the updating includes performing a minimization technique with a cost function having an L2-norm term and an L0-norm term.

Next, processor 1010 may determine weights 1028 associated with features in the updated dictionary of predetermined features based at least in part on the non-invasive measurements.

Moreover, processor 1010 may perform one or more additional actions. For example, processor 1010 may: provide information 1030 (such as weights 1028 and the updated dictionary of predetermined features) to a user or another electronic device via interface circuit 1016, store information 1030 in memory 1014, and/or may present information 1030 on a display 1032 in or associated with computer 116.

While communication between the components in FIGS. 3, 8 and/or 10 is illustrated with unilateral or bilateral communication (e.g., lines having a single arrow or dual arrows), in general a given communication operation may be unilateral or bilateral.

We now further describe the analysis techniques. In the discussion that follows, MRI scans are used as illustrations of the non-invasive measurements in the analysis techniques. Longitudinal health tracking with MRI requires participants to receive repetitive scans. However, MRI was originally designed as a qualitative modality optimized for acute diagnostics. It was not designed to measure or quantify longitudinal changes accurately in anatomical features, structures or tissue properties. The disclosed analysis techniques address these problems. In the process, the analysis techniques also may improve the accuracy of the MRI measurements and may reduce the measurement or scan time and/or the runtime needed to detect the changes.

For a given individual, shared information among MRI scans or exams may accelerate and enhance future MRI scans. Some existing approaches attempt to accelerate longitudinal analysis of MRI scans with historical information. These existing approaches typically require a pixel-wise registration and often fail to capture new or changed anatomical features. The disclosed analysis techniques leverage the previous or prior MRI information in a model-based paradigm. Notably, the historical information may be modeled as a sparsifying basis on which the newer MRI scan can be compressed. In some embodiments, a stochastic protocol optimization technique and/or a self-adaptive compressed sensing reconstruction technique are used to restore the image (either or both of these techniques are sometimes referred to as 'delta imaging'). More generally, delta imaging may include a collection of advanced signal acquisition and reconstruction strategies that enables ultra-fast longitudinal health tracking using one or more previous MRI measurements as priors.

Delta imaging may provide a robust, incremental approach to accelerate or reduce the time needed to perform longitudinal MRI exams with a solid model of the dynamics between MRI exams. In some embodiments, delta imaging may include building a dictionary of (sub-domain, e.g., with limited support) geometrical features that can represent the expected geometrical features in the current (to be acquired) MRI scan. This dictionary may be developed or constructed from previous MRI scans of the individual and/or previous MRI scans of one or more different individuals. Moreover, delta imaging may include building or computing a (spatial and/or frequency-domain) sampling pattern (which may be optimal). The combination of the sampling pattern and the dictionary-based reconstruction may achieve faster (or optimal) MRI scan time given a target image quality. Furthermore, delta imaging may include building or computing a longitudinal sampling pattern(s), with the goal of building a digital twin (or baseline model) of an individual and efficiently capturing the differences (delta) in subsequent MRI scans of this individual. Note that 'efficiently' may include reducing or minimizing the acquisition time (or the amount of time the individual spends inside an MR scanner). For example, a whole body MRI scan may take 15 min or may take less than 10 min. In some embodiments, delta imaging may be adaptive to multi-contrast setting.

Thus, in some embodiments, the analysis techniques may accelerate MRI signal acquisitions based at least in part on one or more prior MRI scans of the same individual, which may have been acquired weeks, months or years earlier. At least one of the prior MRI scans may include a 'slow scan' (e.g., a mildly undersampled or a fully sampled acquisition). Note that a dictionary of geometrical features may be constructed based at least in part on the prior MRI scan(s), which may be used as a sparsifying transformation in a compressed sensing image reconstruction technique.

In some embodiments, image registration may be used to co-register the prior MRI scans with the current MRI scan. However, in other embodiments, image registration may not be needed. Moreover, in some embodiments, data from prior MRI scans may be used to determine an improved or an optimal sampling pattern for the current MRI scan. An optimal sampling may include a set of sampling coordinates that maximizes information content, given a prescribed number of samples (the duration of the scan).

Furthermore, depending on whether the acquisition strategy is based at least in part on Cartesian sampling or not, the optimization of the sampling pattern may include a combinatorial (discrete or subset selection problem) or a continuous optimization problem. For example, in some embodiments, a two-dimensional (2D) on-grid sampling pattern in the x-y plane may be optimized with the z-axis fully sampled. However, in other embodiments, three-dimensional (3D) non-Cartesian sampling may be used for full sampling efficiency and for improved image quality under a ultra-high acceleration ratio. Note that the on-grid sampling pattern may be a 0-1 or categorical problem. Therefore, in these embodiments, the update may not take advantage of the gradient. In comparison with other subset selection problems, the cost of evaluating the new subset (sampling pattern) in the analysis techniques (which is the image reconstruction quality) may be high. Additionally, the sampling pattern may be optimized jointly with the reconstruction technique. Stated differently, the sampling pattern may be optimal for a specific reconstruction strategy, and different reconstruction strategies may result in different sampling patterns.

In some embodiments, the prior MRI scans may have been acquired from different individuals, but from the same portion of the human body. Moreover, in some embodiments, N prior MRI scans (where N is a non-zero integer) may be used to learn the sparsifying transform, where no more than (N−1) MRI scans are from different individuals and at least one is a previous MRI scan of the current individual. In these embodiments, the previous MRI scan from the current individual may be an accelerated acquisition.

Note that after the $M^{th}$ MRI scan of one individual (where M is a non-zero integer), the sparsifying transform of the $(M+1)^{th}$ MRI scan may include information from some or all of the previous MRI scans. Stated differently, initially the dictionary may be learned exclusively from different individuals (e.g., when there are no available prior MRI scans of the current individual), and the computer system may incrementally update an individual-specific dictionary each time the current individual goes through an MRI exam based at least in part on initial dictionary from the different individuals.

Moreover, in some embodiments, program instructions executed by the computer system may adaptively learn that extended or large changes are present in the current MRI scan, the delta scan may be aborted and instead the system may resort to a traditional (slower) baseline MRI scan. In these embodiments, a blind dictionary-based reconstruction may be adopted, where 'blind' indicates that the dictionary is only learned from the current MRI scan on the current individual. Alternatively, other MRI techniques (such as more traditional MRI techniques) may be used.

Figure 11:
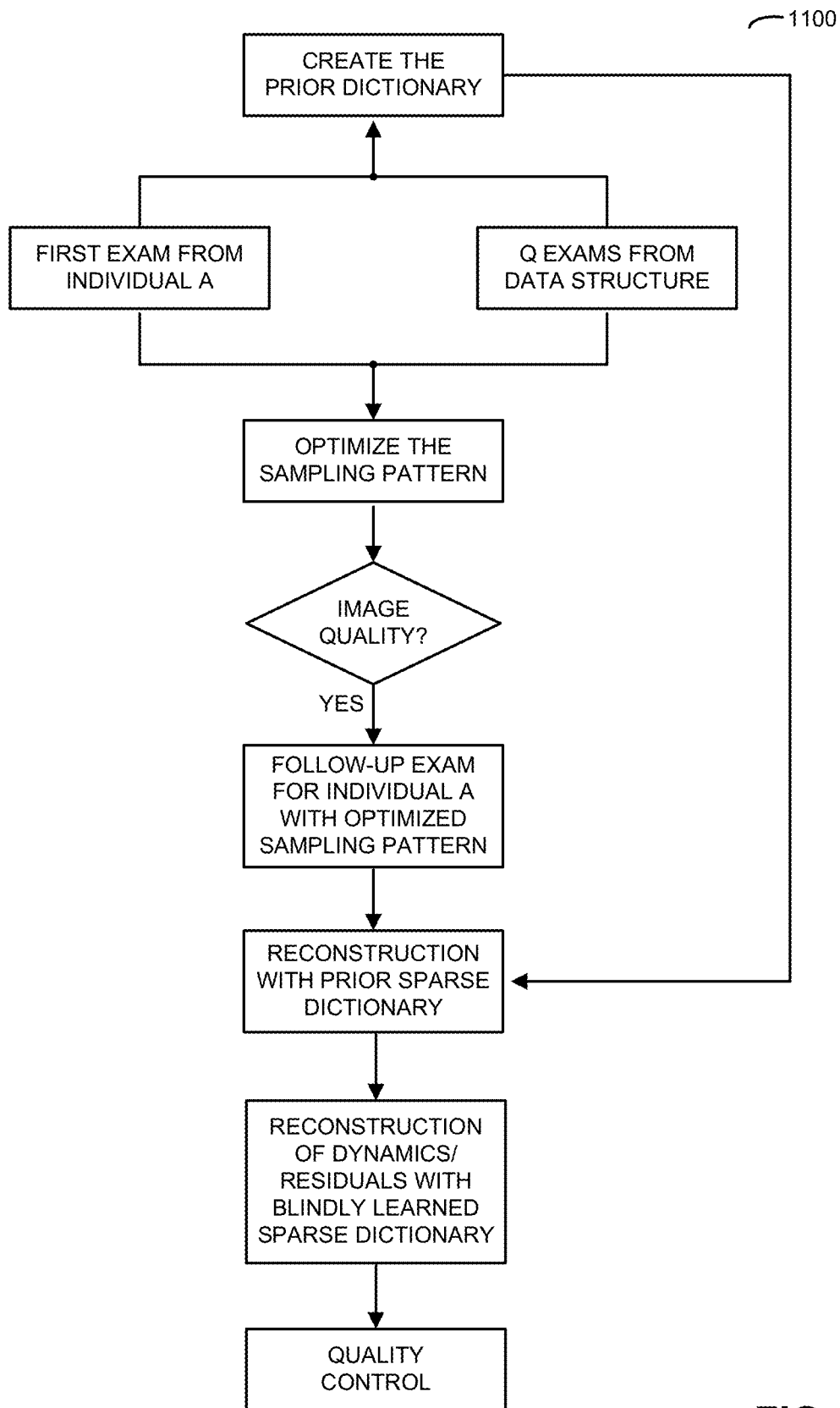
FIG. 11 is a flow diagram illustrating an example of a method for performing a sparsity technique in accordance with an embodiment of the present disclosure.

An example of the analysis techniques is shown in FIG. 11, which presents a flow diagram illustrating an example of a method 1100 for performing a sparsity technique. Note that sampling pattern (or trajectory) optimization may be computed based at least in part on a first MRI scan. MRI may acquire MR signals in the frequency domain (k-space), where constellations stand for energy distribution. Moreover, longitudinal MRI scans for the same individual may share a similar energy distribution (in the signal domain). Furthermore, the image quality may be assessed using a validation set.

The sampling pattern may be optimized based at least in part on the previous MRI exams using a stochastic greedy technique to improve the signal sampling efficiency given a fixed acquisition time. This optimization may maximize the information content of the next sampling point given a fixed number of sampling points. In some embodiments, the stochastic greedy technique may be based at least in part on bias-accelerated subset selection or BASS (from New York University School of Medicine, of New York, New York). Note that that BASS may include or introduce more heuristics, or bias to reduce the number of iterations. In some embodiments, hyper-parameter tuning may take 100 iterations with K equal to 200.

Improvements relative to BASS may include that the use of patch-based reconstruction to replace the compressed-sensing reconstruction as the image restoration technique.

Moreover, another improvement relative to BASS may include that in the expression $$r_k = \frac{1}{N_i N_c} \sum_{i=1}^{N_i} \frac{\sum_{c=1}^{N_c} |[e_{i,c}]_k|^2 + \delta}{\sum_{c=1}^{N_c} |[m_{i,c}]_k|^2 + \delta}$$

the denominator may be smoothened by an averaging filter to counteract the influence of noise. Furthermore, in order to ensure convergence, the looping criterion in BASS is modified with an updated criterion that 'if $|\Omega'| \neq M$, $\Omega$ becomes $\Omega'$', where $\Omega$ is a subset (of size M) of N sample points (which is sometimes referred to as a 'sampling pattern' or SP), and $\Omega'$ is the union of a set of new sample points ($\Omega_a$) and the previous state $\Omega$ removed from a set of sample points in $\Omega_r$. Note that the updated criterion compares the cardinality (the number of elements) of the new constructed set $\Omega'$ with M (the target number of sample points). Thus, when $|\Omega'| \neq M$, we always accept $\Omega'$ and assign it to $\Omega$. Alternatively, when $|\Omega'|=M$, we conditionally accept $\Omega'$ only if it reduces the cost function with respect to $\Omega$.

Additionally, reconstruction may be performed using priors. Notably, MIll images (and, in particular, the changes between MIll images) are typically sparse on a certain transform. Many existing compressed sensing-based techniques often use a fixed and heuristic transform, such as wavelets. For example, in some existing techniques for optimizing sampling patterns and reconstruction for longitudinal analysis of Mill, the sampling pattern optimization may not involve stochastic optimization. Instead, these existing techniques typically assume that the optimal sampling pattern is a stochastic process with a predetermined and empirical density distribution (which may be modelled as a polynomial function with a decay rate that depends on the distance from the origin of the k-space plane). Furthermore, in these existing techniques, the reconstruction usually assumes that both images are sparse in the same wavelet space. Therefore, the sparsifying transform may be a standard wavelet transform (such as a discrete wavelet transform or DWT). Consequently, the sparsifying transform may not be adaptive to the anatomy of the subject. This assumption may not explicitly disentangle the static (such as common features between the two MRI scans) and the dynamic (such as new information or anatomical changes) information.

In the disclosed analysis techniques, the analysis may adaptively learn the sparsifying transform from the previous near-fully-sampled MRI exams. The unchanged/static information in the subsequent MRI scans may be sparse on this transform. Furthermore, the anatomical change may be represented by an adaptively learned sparsifying transform. The disclosed two-stage compressed sensing may effectively use the historical information and may track the dynamic information.

We now describe embodiments of the model-based reconstruction. Notably, in the analysis techniques, the estimated image may be modelled as the combination of two components: historical information, which is formulated as a dictionary (and the corresponding sparse code, $D_1$ and $Z_1$) learned from the first Q MRI exams (where Q is a non-zero integer); and dynamic information, which may be poised as a blindly adaptive dictionary ($D_2$). Stated differently $$\arg\min_{D_2,Z_1,Z_2} (\|Ax - y\|_2^2 + vR(x), \tag{1}$$

where v is a regularization parameter and $$R(x) = \min_{D_2,Z_1,Z_2} (\|Px - D_1 Z_1 - D_2 Z_2\|_2^2 + \lambda_1^2 \|Z_1\|_0 + \lambda_2^2 \|Z_2\|_0. \tag{2}$$

Eqns. 1 and 2 describe the disclosed reconstruction. Eqn. 1 is an abstract expression of model-based MRI reconstruction. A is an MRI forward model. The first term (data consistency) in Eqn. 1 is the maximum likelihood/maximum a posteriori probability (ML/MAP) estimator of y, because it may be assumed that the noise in the signal space is Gaussian. R(x) is a regularizer, which may reflect statistical image characteristics (such as a prior density). In the disclosed analysis techniques, the signal may be assumed to be sparse on two dictionaries, D1 and D2 (where D2 may track the changed or new anatomical features). Note that P is the patch operator that decomposes the image into local patches (which may be concatenated as columns). For example, the patch operator P may extract each 6×6 patch from an original 256×256 pixel image. The patches may overlap, and each pixel may appear in as many as 36 different (overlapping)

patches. Consequently, the dictionaries D1 and D2 may include a set of geometrical features with a support limited to the size of each patch (e.g., one element of a given dictionary may represent a feature defined on 6×6 support). Moreover, each column of $Z_1$ and Z2 may be the sparse code corresponding to an image patch. Furthermore, note that the 0-norm may counts the number of non-zero elements, instead of being the induced 0-norm (rank).

Furthermore, $$\arg \min_{D_1, Z_1} \left( \|Px - D_1 Z_1\|_2^2 + \lambda_1^2 \|Z_1\|_0 \right). \quad (3)$$

In order to get $D_1$ from the previous Q MRI exams, one approach may be to optimize Eqn. 3, in which x is the conjugate phase reconstruction of fully-sampled y, and which may be assumed to be noiseless. Optimization of Eqn. 3 may result in a good sparsifying transform $D_1$ by removing the interference of noise and aliasing artifacts. Another option is more brute-force-ish. Notably, use patches from an anatomical data structure or database, and each column of $Z_1$ then becomes a one-element vector. To make this approach more robust, each dictionary atom may be normalized, with phase extracted. Moreover, the block matching may be applied after a discrete cosine transform (DCT) and thresholding, to counteract the influence of noise. (One question that may occur at this point is whether $D_1$ is required to be co-registered to the newer MRI scan. Based on experiment, the analysis techniques may be tolerant to mild misregistration, and the registration from central k-space (low-res image) may be sufficient). Note that Eqn. 2 is a non-convex and non-smooth problem because of the 0-norm. In some embodiments, a two-stage strategy is adopted or used. First, optimize x and $Z_1$ iteratively, and then x, $D_2$ and $Z_2$. In each stage, an augmented Lagrangian-like optimization technique may be used. The sub-step minimizing 0-norm may use an improved iterative hard-thresholding technique (such as sum of outer product or SOUP). Thus, the optimization may alternate between the minimization of the 'data-consistency' term (which may be solved using conjugate gradient) and block-matching. In some embodiments, it may take 5-10 iterations until convergence.

Figure 12:
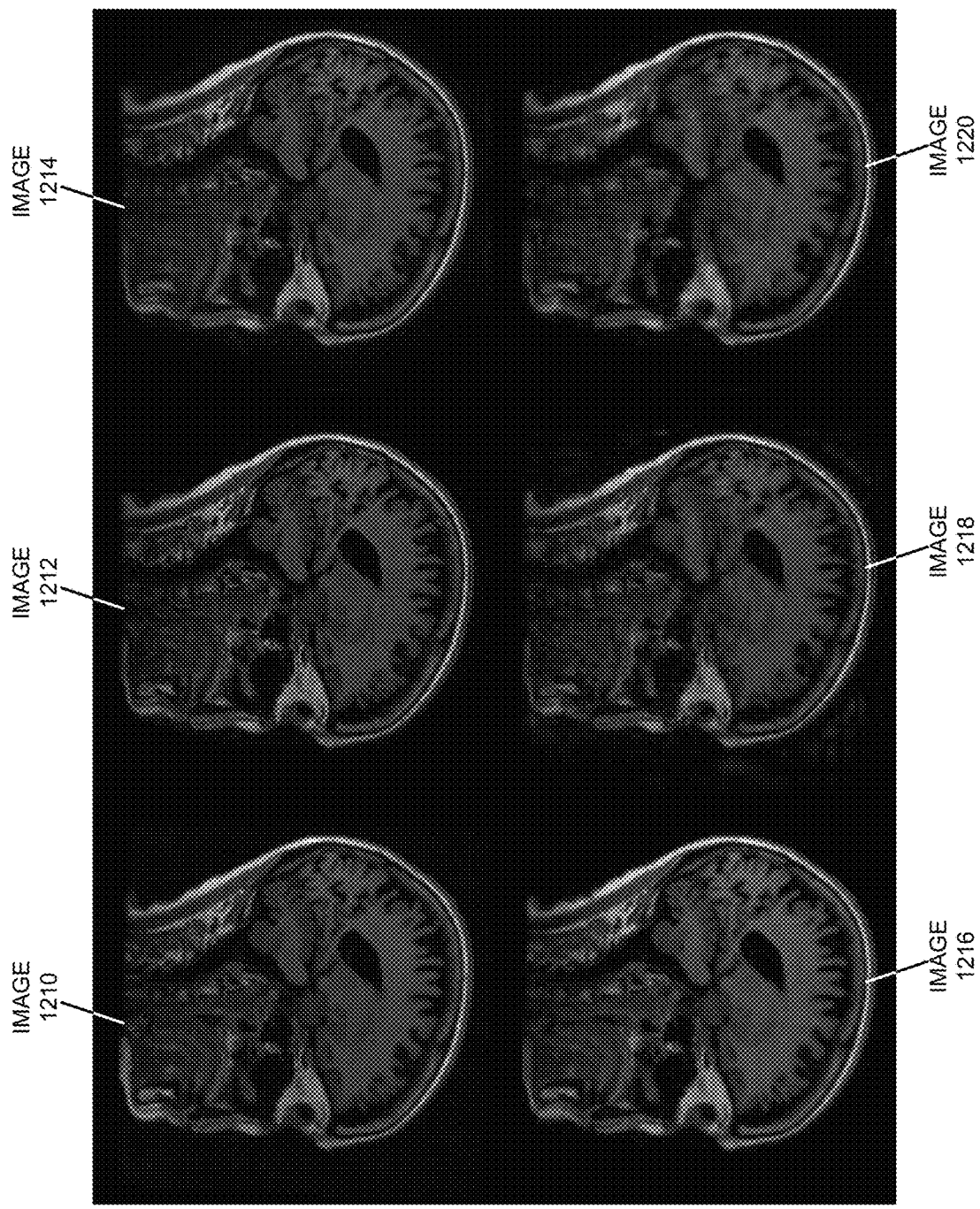
FIG. 12 is a drawing illustrating examples of image reconstructions from sparse representations of MRI data in accordance with an embodiment of the present disclosure.
Figure 13:
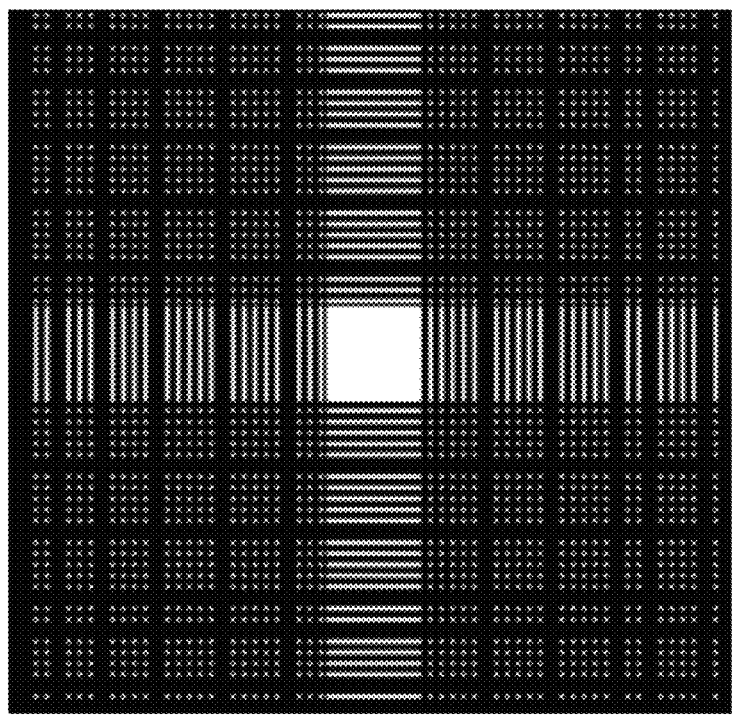
FIG. 13 is a drawing illustrating an example of a sampling pattern used in FIG. 12 in accordance with an embodiment of the present disclosure.

FIG. 12 presents a drawing illustrating examples of image reconstructions from sparse representations of MRI data in accordance with an embodiment of the present disclosure. Notably, image 1210 may be a first MRI exam, image 1212 may be a second MRI exam (with compressed sensing or CS reconstruction using 2.5× undersampling), image 1214 uses delta-imaging reconstruction, image 1216 uses longitudinal adaptive CS (LACS), image 1218 uses L1-wavelets reconstruction, and image 1220 uses blind CS reconstruction. FIG. 13 presents a drawing illustrating an example of a sampling pattern used with image 1214 in FIG. 12.

Figure 14:
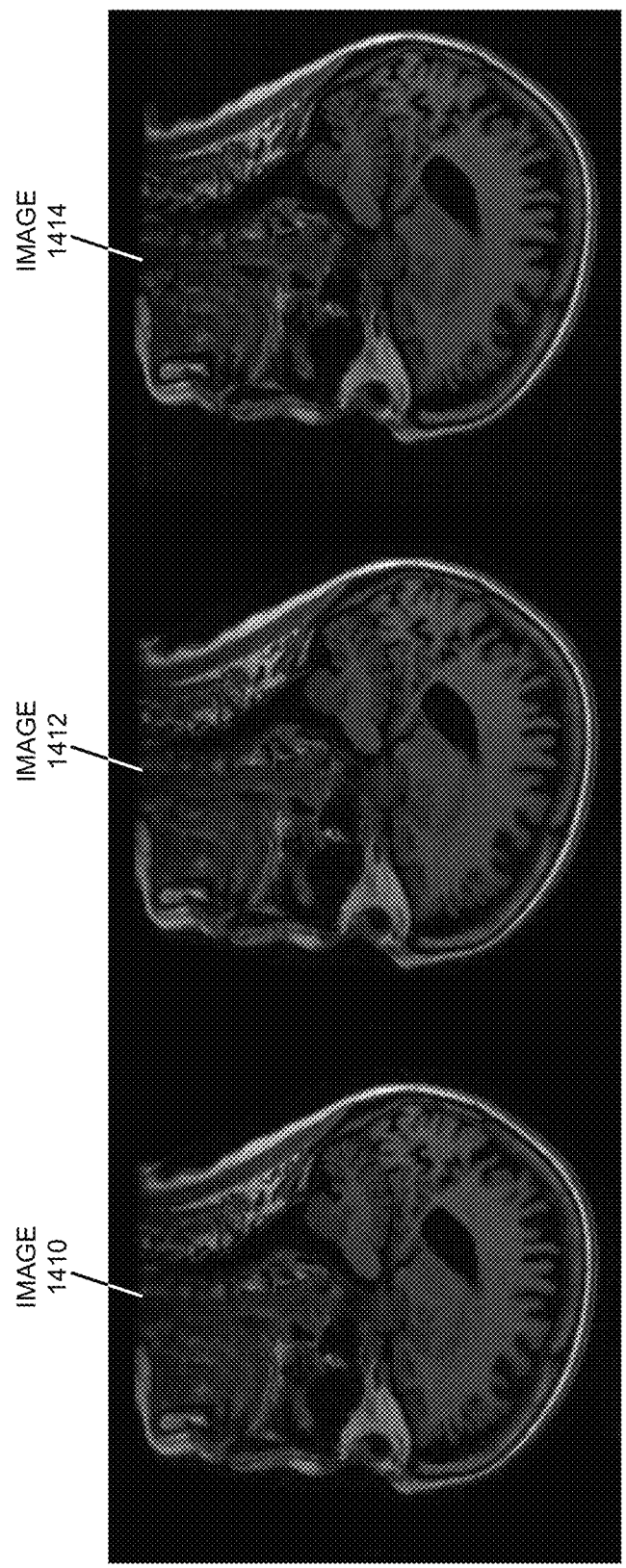
FIG. 14 is a drawing illustrating examples of images using different sampling patterns with MRI data in accordance with an embodiment of the present disclosure.
Figure 15:
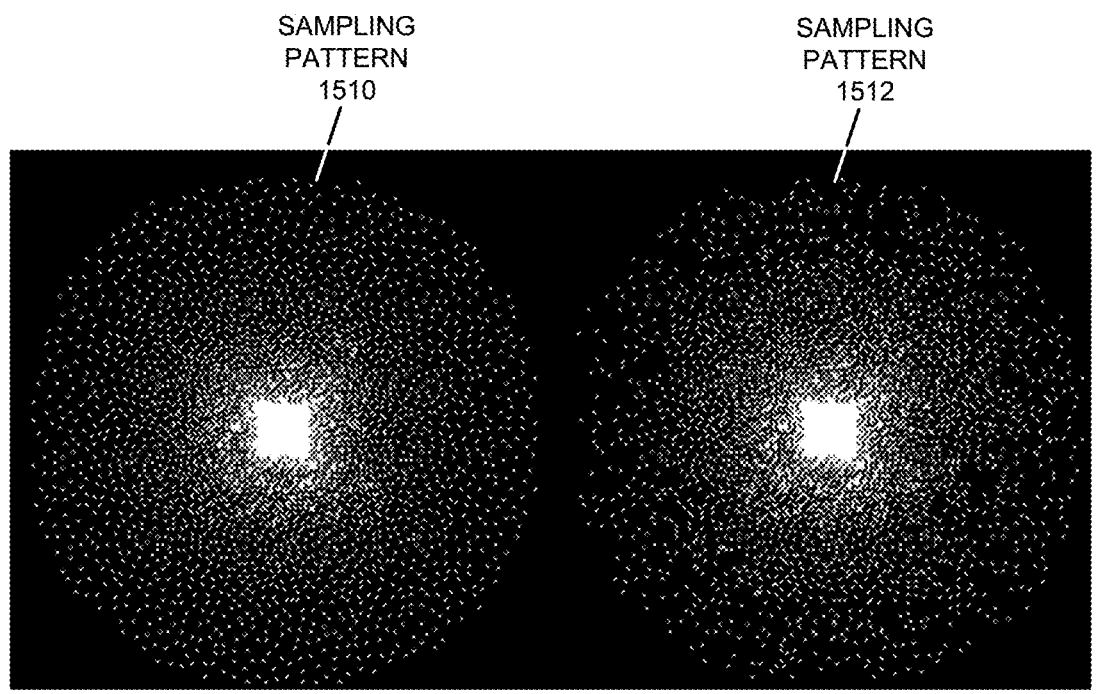
FIG. 15 is a drawing illustrating examples of sampling patterns in accordance with an embodiment of the present disclosure.

FIG. 14 presents a drawing illustrating examples of images using different sampling patterns with MRI data in accordance with an embodiment of the present disclosure. Notably, image 1410 is fully sampled, image 1412 uses variable density Poisson-disk sampling, and image 1414 uses an optimized sampling pattern. FIG. 15 presents a drawing illustrating examples of k-space sampling patterns, including sampling pattern 1510 and sampling pattern 1512.

Figure 16:
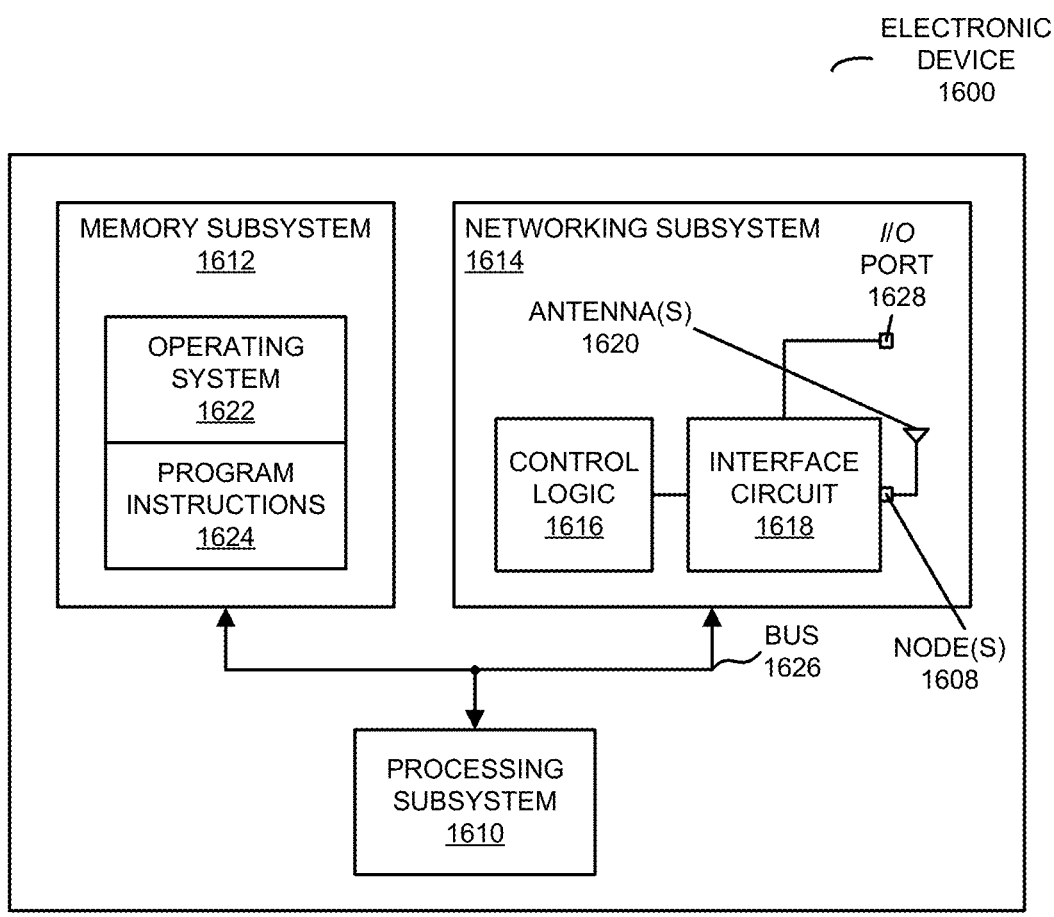
FIG. 16 is a block diagram illustrating an example of an electronic device in accordance with an embodiment of the present disclosure.

We now further describe an electronic device that performs at least some of the operations in the embodiments of the computation techniques and/or the analysis techniques. FIG. 16 presents a block diagram illustrating an electronic device 1600 in system 100 (FIG. 1), such as computer 116 (FIG. 1) or another of the computer-controlled components in system 100, such as source 110 or measurement device 114 (FIG. 1). This electronic device includes a processing subsystem 1610, memory subsystem 1612, and networking subsystem 1614. Processing subsystem 1610 may include one or more devices configured to perform computational operations and to control components in system 100 (FIG. 1). For example, processing subsystem 1610 may include one or more microprocessors or central processing units (CPUs), one or more graphics processing units (GPUs), application-specific integrated circuits (ASICs), microcontrollers, programmable-logic devices (such as a field programmable logic array or FPGA), and/or one or more digital signal processors (DSPs).

Memory subsystem 1612 may include one or more devices for storing data and/or instructions for processing subsystem 1610 and networking subsystem 1614. For example, memory subsystem 1612 may include dynamic random access memory (DRAM), static random access memory (SRAM), and/or other types of memory. In some embodiments, instructions for processing subsystem 1610 in memory subsystem 1612 include one or more program modules or sets of instructions (such as program instructions 1624), which may be executed in an operating environment (such as operating system 1622) by processing subsystem 1610. Note that the one or more computer programs may constitute a computer-program mechanism or a program module (i.e., software). Moreover, instructions in the various modules in memory subsystem 1612 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1610.

In addition, memory subsystem 1612 may include mechanisms for controlling access to the memory. In some embodiments, memory subsystem 1612 includes a memory hierarchy that comprises one or more caches coupled to a memory in electronic device 1600. In some of these embodiments, one or more of the caches is located in processing subsystem 1610.

In some embodiments, memory subsystem 1612 is coupled to one or more high-capacity mass-storage devices (not shown). For example, memory subsystem 1612 may be coupled to a magnetic or optical drive, a solid-state drive, or another type of mass-storage device. In these embodiments, memory subsystem 1612 may be used by electronic device 1600 as fast-access storage for often-used data, while the mass-storage device is used to store less frequently used data.

In some embodiments, memory subsystem 1612 includes a remotely located archive device. This archive device can be a high-capacity network attached mass-storage device, such as: network attached storage (NAS), an external hard drive, a storage server, a cluster of servers, a cloud-storage provider, a cloud-computing provider, a magnetic-tape backup system, a medical records archive service, and/or another type of archive device. Moreover, processing subsystem 1610 may interact with the archive device via an application programming interface to store and/or access information from the archive device. Note that memory subsystem 1612 and/or electronic device 1600 may be compliant with the Health Insurance Portability and Accountability Act.

Figure 17:
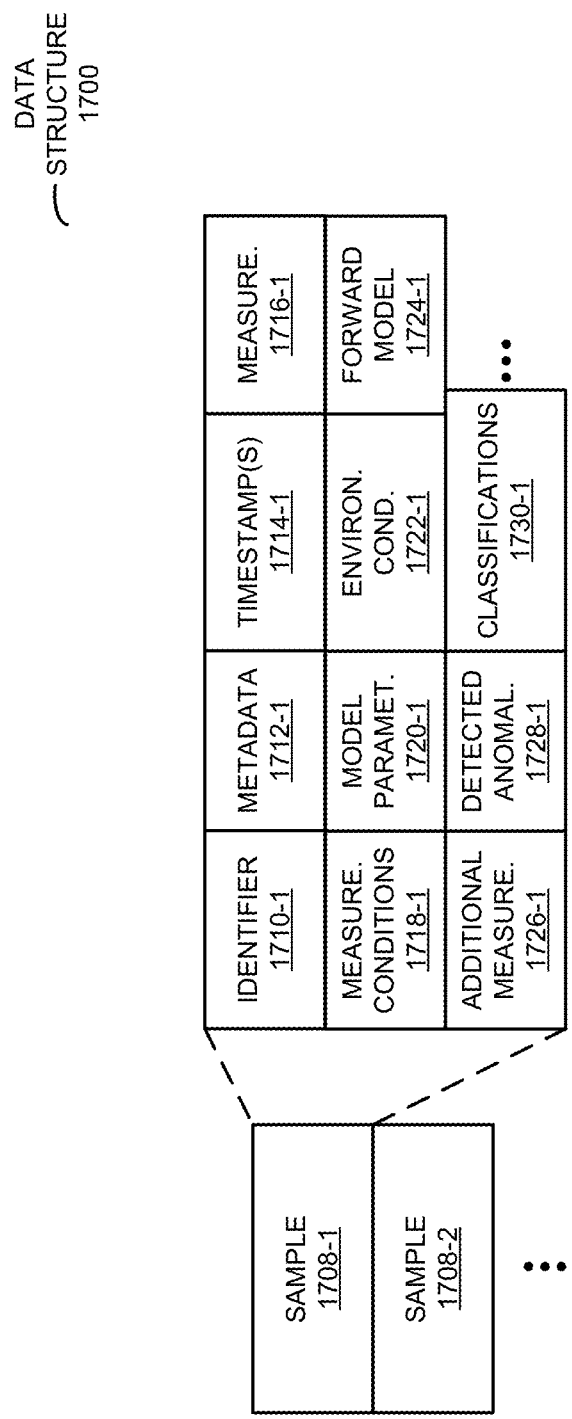
FIG. 17 is a drawing illustrating an example of a data structure that is used by the electronic device of FIG. 14 in accordance with an embodiment of the present disclosure.

An example of the data stored (locally and/or remotely) in memory subsystem 1612 is shown in FIG. 17, which presents a drawing illustrating an example of a data structure 1700 that is used by electronic device 1600 (FIG. 16). This data structure may include: an identifier 1710-1 of sample 1708-1 (such as an individual), metadata 1712 (such as age, gender, biopsy results and diagnosis if one has already been made, other sample information, demographic information, family history, etc.), timestamps 1714 when data was acquired, received measurements 1716 (such as MR signals and, more generally, raw data), excitation and measurement conditions 1718 (such as an external magnetic field, an optional gradient, an RF pulse sequence, an MR apparatus, a location, machine-specific characteristics such as magnetic-field inhomogeneity, RF noise and one or more other system imperfections, signal-processing techniques, registration information, synchronization information such between measurements and a heartbeat or breathing pattern of an individual, etc.), and/or determined model parameters 1720 (including voxel sizes, speed, resonant frequency or a type of nuclei, $T_1$ and $T_2$ relaxation times, segmentation information, classification information, etc.), environmental conditions 1722 (such as the temperature, humidity and/or barometric pressure in the room or the chamber in which sample 1708-1 was measured), forward model 1724, one or more additional measurements 1726 of physical properties of sample 1708-1 (such as weight, dimensions, images, etc.), optional detected anomalies 1728 (which may include particular voxel(es) associated with the one or more of detected anomalies 1728), and/or optional classifications 1730 of the one or more detected anomalies 1728. Note that data structure 1700 may include multiple entries for different measurements.

In one embodiment, data in data structure 1700 is encrypted using a block-chain or a similar cryptographic hash technique to detect unauthorized modification or corruption of records. Moreover, the data can be anonymized prior to storage so that the identity of an individual associated with a sample is anonymous unless the individual gives permission or authorization to access or release the individual's identity.

Referring back to FIG. 16, networking subsystem 1614 may include one or more devices configured to couple to and communicate on a wired, optical and/or wireless network (i.e., to perform network operations and, more generally, communication), including: control logic 1616, an interface circuit 1618, one or more antennas 1620 and/or input/output (I/O) port 1628. (While FIG. 16 includes one or more antennas 1620, in some embodiments electronic device 1600 includes one or more nodes 1608, e.g., a pad or connector, which can be coupled to one or more antennas 1620. Thus, electronic device 1600 may or may not include one or more antennas 1620.) For example, networking subsystem 1614 can include a Bluetooth networking system (which can include Bluetooth Low Energy, BLE or Bluetooth LE), a cellular networking system (e.g., a 3G/4G/5G network such as UMTS, LTE, etc.), a universal serial bus (USB) networking system, a networking system based on the standards described in IEEE 802.11 (e.g., a Wi-Fi networking system), an Ethernet networking system, and/or another networking system.

Moreover, networking subsystem 1614 may include processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for network subsystem 1614.

Moreover, in some embodiments a 'network' between components in system 100 (FIG. 1) does not yet exist. Therefore, electronic device 1600 may use the mechanisms in networking subsystem 1614 for performing simple wireless communication between the components, e.g., transmitting advertising or beacon frames and/or scanning for advertising frames transmitted by other components.

Within electronic device 1600, processing subsystem 1610, memory subsystem 1612, networking subsystem 1614 may be coupled using one or more interconnects, such as bus 1626. These interconnects may include an electrical, optical, and/or electro-optical connection that the subsystems can use to communicate commands and data among one another. Although only one bus 1626 is shown for clarity, different embodiments can include a different number or configuration of electrical, optical, and/or electro-optical connections among the subsystems.

Electronic device 1600 may be (or can be) included in a wide variety of electronic devices. For example, electronic device 1600 may be included in: a tablet computer, a smartphone, a smartwatch, a portable computing device, a wearable device, test equipment, a digital signal processor, a cluster of computing devices, a laptop computer, a desktop computer, a server, a subnotebook/netbook and/or another computing device.

Although specific components are used to describe electronic device 1600, in alternative embodiments, different components and/or subsystems may be present in electronic device 1600. For example, electronic device 1600 may include one or more additional processing subsystems, memory subsystems, and/or networking subsystems. Additionally, one or more of the subsystems may not be present in electronic device 1600. Moreover, in some embodiments, electronic device 1600 may include one or more additional subsystems that are not shown in FIG. 16.

Although separate subsystems are shown in FIG. 16, in some embodiments, some or all of a given subsystem or component can be integrated into one or more of the other subsystems or components in electronic device 1600. For example, in some embodiments program instructions 1624 are included in operating system 1622. In some embodiments, a component in a given subsystem is included in a different subsystem. Furthermore, in some embodiments electronic device 1600 is located at a single geographic location or is distributed over multiple different geographic locations.

Moreover, the circuits and components in electronic device 1600 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 1614 (such as a radio) and, more generally, some or all of the functionality of electronic device 1600. Moreover, the integrated circuit may include hardware and/or software mechanisms that are used for transmitting wireless signals from electronic device 1600 and receiving signals at electronic device 1600 from other components in system 100 (FIG. 1) and/or from electronic devices outside of system 100 (FIG. 1). Aside from the mechanisms herein described, radios are generally known in the art and hence are not described in detail. In general, networking subsystem 1614 and/or the integrated circuit can include any number of radios. Note that the radios in multiple-radio embodiments function in a similar way to the radios described in single-radio embodiments.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both.

In addition, in some of the preceding embodiments there are fewer components, more components, a position of a component is changed and/or two or more components are combined.

While the preceding discussion illustrated the computation technique to solve a vector wave equation, in other embodiments the computation technique may be used to solve a scalar equation. For example, an acoustic wave equation may be solved in an arbitrary inhomogeneous media based on ultrasound measurements using a forward model. (Thus, in some embodiments the excitation may be mechanical.) Note that the acoustic coupling in ultrasound measurements can dependent on the operator (i.e., the ultrasound measurements may be pressure dependent). Nonetheless, a similar approach may be used to: improve ultrasound imaging, determine 3D structure, facilitate improved presentation, etc.

In the preceding description, we refer to 'some embodiments.' Note that 'some embodiments' describes a subset of all of the possible embodiments, but does not always specify the same subset of embodiments. Moreover, note that numerical values in the preceding embodiments are illustrative examples of some embodiments. In other embodiments of the computation techniques and/or the analysis techniques, different numerical values may be used.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A method of performing a sparsity technique, comprising:
   by a computer system:
   updating a dictionary of predetermined features based at least in part on non-invasive measurements performed on an individual and historical non-invasive measurements;
   determining weights associated with features in an updated dictionary of predetermined features based at least in part on the non-invasive measurements;
   computing or selecting a sampling pattern based at least in part on the non-invasive measurements and the historical non-invasive measurements;
   obtaining an image of at least a portion of the individual by performing additional non-invasive measurements based at least in part on the computed or selected sampling pattern, wherein the image comprises a sub-sampled or a compressed image; and
   reconstructing a second image based at least in part on the image, the updated dictionary of predetermined features and the determined weights.

2. The method of claim 1, wherein the non-invasive measurements and the historical non-invasive measurements comprise or correspond to magnetic-resonance (MR) measurements.

3. The method of claim 1, wherein the updating comprises performing a minimization technique with a cost function having an L2-norm term and an L0-norm term.

4. The method of claim 1, wherein the non-invasive measurements and the historical non-invasive measurements comprises magnetic-resonance (MR) parameters associated with voxels in the individual.

5. The method of claim 4, wherein the MR parameters comprise: a density of a type of nuclei, a longitudinal relaxation time along a direction parallel to an external magnetic field and a transverse relaxation time along a direction perpendicular to the external magnetic field.

6. The method of claim 4, wherein the non-invasive measurement comprise at least a component of a magnetization associated with the individual, and the method comprises:
   calculating at least a predicted component of the magnetization for the voxels associated with the individual based at least in part on the measured component of the magnetization, a forward model, an external magnetic field and a radio frequency (RF) pulse sequence; and
   solving an inverse problem by iteratively modifying the MR parameters associated with the voxels in the forward model until a difference between the predicted component of the magnetization and the measured component of the magnetization is less than a predefined value.

7. The method of claim 1, wherein the historical non-invasive measurements are associated with the individual or a group of individuals.

8. The method of claim 7, wherein the group of individuals excludes the individual.

9. The method of claim 1, wherein determining the weights comprises a gradient-descent technique.

10. The method of claim 1, wherein the updated dictionary of predetermined features correspond to a portion of an anatomy of the individual.

11. A computer system, comprising:
    an interface circuit;
    a processor coupled to the interface circuit; and
    memory, coupled to the processor, storing program instructions, wherein, when executed by the processor, the program instructions cause the computer system to perform operations comprising:
       updating a dictionary of predetermined features based at least in part on non-invasive measurements performed on an individual and historical non-invasive measurements;
       determining weights associated with features in the updated dictionary of predetermined features based at least in part on the non-invasive measurements;
       computing or selecting a sampling pattern based at least in part on the non-invasive measurements and the historical non-invasive measurements;

obtaining an image of at least a portion of the individual by performing additional non-invasive measurements based at least in part on the computed or selected sampling pattern, wherein the image comprises a sub-sampled or a compressed image; and reconstructing a second image based at least in part on the image, the updated dictionary of predetermined features and the determined weights.

12. The computer system of claim 11, wherein the non-invasive measurements and the historical non-invasive measurements comprise or correspond to magnetic-resonance (MR) measurements.

13. The computer system of claim 11, wherein the non-invasive measurements and the historical non-invasive measurements comprises magnetic-resonance (MR) parameters associated with voxels in the individual.

14. The computer system of claim 11, wherein the updating comprises performing a minimization technique with a cost function having an L2-norm term and an L0-norm term.

15. The computer system of claim 13, wherein the non-invasive measurement comprise at least a component of a magnetization associated with the individual, and the operations comprise:

calculating at least a predicted component of the magnetization for the voxels associated with the individual based at least in part on the measured component of the magnetization, a forward model, an external magnetic field and a radio frequency (RF) pulse sequence; and solving an inverse problem by iteratively modifying the MR parameters associated with the voxels in the forward model until a difference between the predicted component of the magnetization and the measured component of the magnetization is less than a predefined value.

16. The computer system of claim 11, wherein the historical non-invasive measurements are associated with the individual or a group of individuals; and wherein the group of individuals excludes the individual.

17. The computer system of claim 11, wherein determining the weights comprises a gradient-descent technique.

18. The computer system of claim 11, wherein the updated dictionary of predetermined features correspond to a portion of an anatomy of the individual.

19. A non-transitory computer-readable storage medium for use in conjunction with a computer system, the computer-readable storage medium configured to store a program module that, when executed by the computer system, causes the computer system to perform operations comprising:

updating a dictionary of predetermined features based at least in part on non-invasive measurements performed on an individual and historical non-invasive measurements;

determining weights associated with features in the updated dictionary of predetermined features based at least in part on the non-invasive measurements;

computing or selecting a sampling pattern based at least in part on the non-invasive measurements and the historical non-invasive measurements;

obtaining an image of at least a portion of the individual by performing additional non-invasive measurements based at least in part on the computed or selected sampling pattern, wherein the image comprises a sub-sampled or a compressed image; and reconstructing a second image based at least in part on the image, the updated dictionary of predetermined features and the determined weights.

20. The computer-readable storage medium of claim 19, wherein the non-invasive measurements and the historical non-invasive measurements comprises magnetic-resonance (MR) parameters associated with voxels in the individual.

* * * * *